US009436481B2

(12) United States Patent
Drew

(10) Patent No.: US 9,436,481 B2
(45) Date of Patent: Sep. 6, 2016

(54) RESTORATION OF MEDICAL DEVICE PROGRAMMING

(71) Applicant: Medtronic, Inc., Minneapolis, MN (US)

(72) Inventor: Touby A. Drew, Golden Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 553 days.

(21) Appl. No.: 13/783,514

(22) Filed: Mar. 4, 2013

(65) Prior Publication Data

US 2013/0283030 A1  Oct. 24, 2013

Related U.S. Application Data

(60) Provisional application No. 61/636,809, filed on Apr. 23, 2012.

(51) Int. Cl.
*G06F 9/44* (2006.01)
*G06F 11/14* (2006.01)
*G06F 19/00* (2011.01)

(52) U.S. Cl.
CPC ......... *G06F 9/4421* (2013.01); *G06F 11/1433* (2013.01); *G06F 19/3406* (2013.01)

(58) Field of Classification Search
CPC .............. G06F 8/65; G06F 8/66; G06F 8/67; G06F 8/68
See application file for complete search history.

(56) References Cited

U.S. PATENT DOCUMENTS

| 6,442,433 | B1 | 8/2002 | Linberg |
| 6,665,565 | B1 | 12/2003 | Stomberg et al. |
| 7,096,067 | B2 | 8/2006 | Linberg |
| 7,160,284 | B2 | 1/2007 | Ullestad et al. |
| 7,373,206 | B2 | 5/2008 | Sieracki et al. |
| 7,483,744 | B2 | 1/2009 | Stubbs et al. |
| 8,000,788 | B2 | 8/2011 | Giftakis et al. |
| 8,515,911 | B1* | 8/2013 | Zhou et al. .................. 707/638 |
| 2004/0138724 | A1 | 7/2004 | Sieracki et al. |
| 2005/0049656 | A1* | 3/2005 | Petersen et al. ............... 607/60 |
| 2005/0283198 | A1 | 12/2005 | Haubrich et al. |
| 2006/0080654 | A1* | 4/2006 | Shelton .................... G06F 8/65 717/173 |
| 2006/0161214 | A1 | 7/2006 | Patel |
| 2007/0006222 | A1* | 1/2007 | Maier et al. ................. 717/174 |
| 2008/0027514 | A1* | 1/2008 | DeMulling et al. ........... 607/60 |
| 2009/0005728 | A1* | 1/2009 | Weinert et al. ................ 604/66 |
| 2009/0259216 | A1* | 10/2009 | Drew et al. ............... 604/891.1 |
| 2010/0114206 | A1* | 5/2010 | Kaemmerer et al. ............. 607/5 |
| 2010/0228314 | A1* | 9/2010 | Goetz ............................ 607/41 |

(Continued)

*Primary Examiner* — Jaweed A Abbaszadeh
*Assistant Examiner* — Cheri Harrington
(74) *Attorney, Agent, or Firm* — Shumaker & Sieffert, P.A.

(57) ABSTRACT

Various embodiments concern reprogramming an implantable medical device by an external programmer to operate using a second program version, the second program version replacing a first program version in controlling operation of the implantable medical device. It can be determined whether the implantable medical device will be able to operate using the first program version to deliver therapy according to the first program version if the implantable medical device was to revert back to using the first program version. The implantable medical device can then revert to operational programming from the second program version to the first program version, the first program version saved in memory of the implantable medical device as a restore point while the implantable medical device operates according to the second program version between the reprogramming and reverting of the implantable medical device.

27 Claims, 6 Drawing Sheets

(56) References Cited

U.S. PATENT DOCUMENTS

| | | | |
|---|---|---|---|
| 2010/0306757 A1* | 12/2010 | Becker et al. | 717/170 |
| 2011/0106776 A1* | 5/2011 | Vik | 707/698 |
| 2011/0302564 A1* | 12/2011 | Byers et al. | 717/146 |
| 2012/0096451 A1* | 4/2012 | Tenbarge et al. | 717/170 |
| 2012/0215285 A1* | 8/2012 | Tahmasian et al. | 607/59 |

* cited by examiner

RESTORATION OF MEDICAL DEVICE PROGRAMMING

This application claims priority to provisionally-filed patent application 61/636,809 filed Apr. 23, 2012 which is incorporated herein by reference in its entirety.

TECHNICAL FIELD

The invention relates to medical devices and, more particularly, to medical device programming.

BACKGROUND

Implantable medical devices (IMD) can be implanted subcutaneously in patients to perform various functions. Many implantable medical devices deliver a therapy to treat a condition of the patient. Such therapies can be stimulation therapies or drug infusion therapies, for example.

Clinicians and patients typically communicate with implantable medical devices using external programmers. A clinician may use a clinician programmer to perform advanced setup and diagnostics of the implantable medical device, while a patient programmer typically provides a less feature-rich interface for the patient to interact with the implantable medical device. An external programmer can be used to program an implantable medical device to function according to a physician prescribed regimen of therapy.

SUMMARY

Various embodiments concern a method for reconfiguring an implantable medical device. Such methods can comprise reprogramming an implantable medical device to operate using a second program version, the second program version replacing a first program version in controlling operation of the implantable medical device, the implantable medical device reprogrammed by an external programmer. Such methods can further comprise determining whether the implantable medical device will be able to operate using the first program version to deliver therapy according to the first program version if the implantable medical device was to revert back to using the first program version and reverting operational programming of the implantable medical device from the second program version to the first program version, the first program version saved in memory of the implantable medical device as a restore point while the implantable medical device operates according to the second program version between the reprogramming and reverting of the implantable medical device.

Some of the method embodiments further comprise creating the restore point based on the first program version and saving the restore point in the memory of the implantable medical device. In some of these embodiments the restore point is created during a telemetry session between the implantable medical device and the external programmer, the determining step is performed during the telemetry session, the reprogramming step is performed during the telemetry session, and the restore point is only created if it is determined that the implantable medical device will be able to operate using the first program version to deliver therapy according to the first program version.

Some of the method embodiments further comprise detecting a problematic condition, wherein the reverting step is performed based on the detection of the problematic condition. In some of these embodiments detecting the problematic condition comprises the implantable medical device detecting one or more errors preventing an intended operation of the implantable medical device. In some alternative cases, detecting the problematic condition comprises the implantable medical device receiving an external signal indicating dissatisfaction with operation of the implantable medical device. In some of these embodiments, the determining step is performed based on the detection of the problematic condition, and the reverting step is only performed if the determining step determines that the implantable medical device will be able to operate using the first program version to deliver therapy according to the first program version.

In some of the method embodiments, the determining step further comprises determining which program versions of a plurality of program versions saved in memory of the implantable medical device as a plurality of restore points the implantable medical device will be able to operate to deliver therapy according to each respective program version of the plurality of program versions, and deleting or invalidating any of the plurality of restore points for which the determination step determines that the implantable medical device will not be able to use to operate the implantable medical device to deliver therapy according to the respective program version.

In some of the method embodiments, the determining step comprises determining whether a therapy medium of the implantable medical device which the first program version would use has been changed. In some of the method embodiments, the determining step comprises determining whether a drug stored within the implantable medical device or an electrode configuration has been changed. In some cases, the first program version includes firmware that controls the basic functions of the implantable medical device. In some cases, the first program version includes program instructions that control therapy settings for the implantable medical device. In some cases, reverting operational programming of the implantable medical device from the second program version to the first program version only restores the therapy settings of the first program version and does not change operational logic that controls other functions of the implantable medical device. Some methods include programming the implantable medical device with the first program version, the first program version controlling operation of the implantable medical device until the reprogramming step.

Various system embodiments concern reconfiguring an implantable medical device. Such system embodiments can include an implantable medical device configured to deliver therapy to a patient, the implantable medical device configured to operate according to a first program version loaded on the implantable medical device. Such system embodiments can further include an external programmer, the external programmer configured to reprogram the implantable medical device via telemetry to operate according to a second program version that replaces the first program version in controlling operation of the implantable medical device. System embodiments can further include control circuitry located in either or both of the implantable medical device and the external programmer, the control circuitry configured to determine whether the implantable medical device will be able to operate using the first program version to deliver therapy according to the first program version if the implantable medical device was to revert back to using the first program version, wherein the implantable medical device is configured to revert from operating according to the second program version to operating according to the first program version, the first program version saved in memory of the implantable medical device as a restore point as the implantable medical device operates according to the second program version.

In some of the system embodiments, the control circuitry is configured to create the restore point based on the first program version and save the restore point in memory of the implantable medical device. In some further cases, the control circuitry is configured to create the restore point during a telemetry session between the implantable medical device and the external programmer, the external programmer is configured to reprogram the implantable medical device during the telemetry session, and the control circuitry is configured to create the restore point only if it is determined that the implantable medical device will be able to operate using the first program version to deliver therapy according to the first program version if the implantable medical device was to revert back to using the first program version.

In various system embodiments, the implantable medical device is configured to detect a problematic condition and the implantable medical device is configured to perform the reversion based on the detection of the problematic condition. In some such cases, the implantable medical device is configured to detect the problematic condition by detecting one or more errors preventing intended operation of the implantable medical device. Alternatively, the implantable medical device may be configured to detect the problematic condition by receiving an external signal indicating dissatisfaction with operation of the implantable medical device. In some of these cases, the control circuitry that is configured to determine whether the implantable medical device will be able to operate using the first program version to deliver therapy according to the first program version is located within the implantable medical device and is further configured to perform the determination based on the detection of the problematic condition, and the implantable medical device is configured to revert from operating according to the second program version to operating according to the first program version only if the control circuitry determines that the implantable medical device is able to operate using the first program version.

In various system embodiments, the control circuitry is further configured to determine which program versions of a plurality of program versions saved in memory of the implantable medical device as a plurality of restore points the implantable medical device will be able to operate to deliver therapy according to each respective program version of the plurality of program versions, and delete or invalidate any of the plurality of restore points for which the control circuitry determines that the implantable medical device will not be able to use to operate the implantable medical device to deliver therapy according to the respective program version.

In various system embodiments, the control circuitry is configured to determine whether the implantable medical device will be able to operate using the first program version to deliver therapy according to the first program version by at least determining whether a therapy medium of the implantable medical device that the first program version would use has changed. In various system embodiments, the control circuitry is configured to determine whether the implantable medical device will be able to operate using the first program version to deliver therapy according to the first program version by at least determining whether a drug stored within the implantable medical device or an electrode configuration has changed.

In various system embodiments, the first program version includes firmware that controls the basic functions of the implantable medical device. In various system embodiments, the first program version includes program instructions that control therapy settings for the implantable medical device. In various system embodiments, the reversion of operational programming by the implantable medical device from the second program version to the first program version only restores the therapy settings of the first program version and does not change operational logic that controls the basic functions of the implantable medical device.

Various embodiments concern means for reprogramming an implantable medical device to operate using a second program version, the second program version replacing a first program version in controlling operation of the implantable medical device, means for determining whether the implantable medical device will be able to operate using the first program version to deliver therapy according to the first program version if the implantable medical device was to revert back to using the first program version, and means for reverting operational programming of the implantable medical device from the second program version to the first program version, the first program version saved in memory of the implantable medical device as a restore point while the implantable medical device operates according to the second program version between the reprogramming and reverting of the implantable medical device.

Some embodiments concern a physically embodied (i.e., "non-transitory") computer-readable medium comprising instructions executable by a processor to cause circuitry to reprogram an implantable medical device to operate using a second program version, the second program version replacing a first program version in controlling operation of an implantable medical device, determine whether the implantable medical device will be able to operate using the first program version to deliver therapy according to the first program version if the implantable medical device was to revert back to using the first program version, and revert operational programming of the implantable medical device from the second program version to the first program version, the first program version saved in memory of the implantable medical device as a restore point while the implantable medical device operates according to the second program version between the reprogramming and reverting of the implantable medical device.

The details of one or more examples disclosed herein are set forth in the accompanying drawings and the description below. Other features, objects, and advantages will be apparent from the description and drawings, and from the claims.

DETAILED DESCRIPTION

Figure 1:
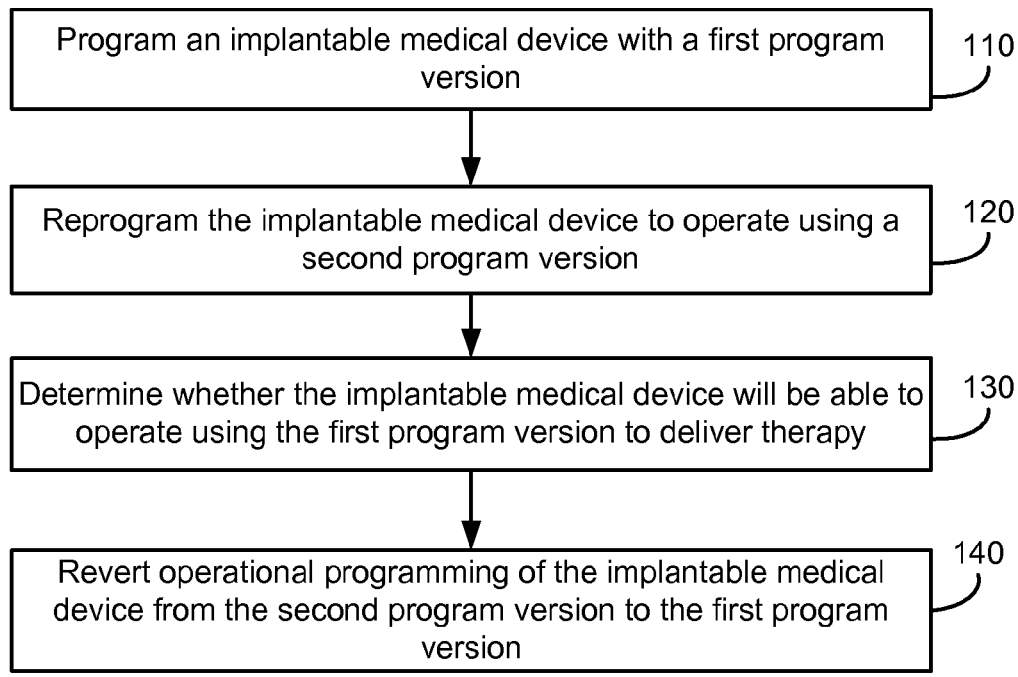
FIG. 1 is a flowchart of a method according to various embodiments for restoring programming in a medical device.

Many implantable medical devices function by the execution of one or more programs by a processor or other logic circuitry located within the implantable medical device. The program instructions may comprise the firmware of the implantable medical device controlling the automated functions of the implantable medical device. An implantable medical device can have memory that stores program instructions that are executable by a processor within the implantable medical device to control the delivery of therapy according to a schedule. In this example, the processor can control therapy delivery circuitry, including the commencement of delivery, the rate of delivery, and the cessation of delivery, among other therapy settings. Additionally or alternatively, other functions can be carried out by circuitry of an implantable medical device, such as sensing of a parameter (e.g., a biological parameter or a self-diagnostic parameter), telemetry of information to and/or from an external device (e.g., a programmer), power management, and device diagnostics, among other functions. Such functions can be performed by the execution of firmware program instructions or other levels of program instructions stored in the implantable medical device.

The circuitry of an implantable medical device performing automated functions can encounter problematic conditions. For example, memory onboard the implantable medical device may become corrupted, compromising information stored within the implantable medical device. If program instructions are corrupted, then the implantable medical device may fail to operate as intended. If program instructions affecting therapy settings (e.g., at the firmware or the therapy program level) are corrupted, then the ability to deliver therapy may be diminished or lost.

Besides the corruption of data, other errors can compromise the function of an implantable medical device. For example, an external programmer may place an incompatible, conflicting, or otherwise mismatched program version on an implantable medical device or program the implantable medical device with settings that are incompatible with the current state of the implantable medical device. One of many hardware components may fail. In these cases, part of the functionality of an implantable medical device, or all of the functionality of the implantable medical device, may be compromised, jeopardizing therapy delivery.

Computing devices generally have several options for dealing with corrupted program instructions or other errors that prevent the computing devices from functioning as intended. For example, a computing device can shut down after generating an error message. A temporary shutdown can sometimes be performed in an effort to reboot and reload a problematic program, hopefully with better results. Some computing devices can continue executing working programs while refraining from using malfunctioning programs. Some devices, especially networked devices, can have a diagnostic check performed by another device. Some devices are complex enough to execute self-diagnostics and perform repairs.

However, these options for handling errors may have drawbacks in some applications. A reboot may not permanently clear all errors, such as where the error pertains to corrupted program instructions. The shutting down of an implantable medical device ceases the function of the device, which may have been providing a critical therapy to the patient. Likewise, other actions that can cause cessation of a function may not be ideal in an implantable environment. Also, in order to avoid errors, minimize supporting hardware, and avoid excessive power consumption, the designs of implantable medical devices can be simplified as much as possible, which can cause some designs to forgo complex self-diagnostic and repair capabilities.

This disclosure presents several options for recovering from errors in implantable medical devices so that functionality can be preserved and, in some cases, therapy can be continued. Various embodiments concern the storing of select restore points on an implantable medical device facilitated by an external programmer, the restore points based on previous program versions of the implantable medical device. An implantable medical device can revert to one of the restore points if an error is encountered by the implantable medical device that compromises the intended function of the implantable medical device. In reverting to a previous program version, the implantable medical device may be able to overcome errors that were introduced by reprogramming of the implantable medical device that took place after the establishment of the restore point or introduced some other way. As discussed herein, various embodiments can automatically assess whether to create a restore point and/or whether to revert to a restore point.

Restore points may first be established based on compatibility between a current program version or a program version currently being replaced, and a current or expected enacted state of the implantable medical device. For example, compatibly may be based on the same drug being used in an implantable drug pump in the prior program version, on which the restore point is based, and a current program version needing replacement. In this way, restore points may only be generated and retained in an implantable medical device if there is some compatibility between a current state of the device and a future expected state of the device (e.g., the device will be loaded with the same drug). Additionally or alternatively, the implantable medical device may check whether one or more saved restore points are compatible with the current state of the implantable medical device, such as a match between the drug used in a previous restore point and the drug currently within the reservoir of the implantable medical device.

Assessing the compatibility between a current or previous device state on which a restore point is based, and a current or future device state, for which a restore point can be enacted, can help avoid serious mistakes. For example, a previous program version can control an implantable medical device to dispense a drug from its reservoir at a particular rate. The drug might be relatively weak (e.g., with a low concentration) and accordingly the delivery rate setting at which the previous program version controlled the drug to be delivered might be relatively high. A restore point, stored within the memory of the implantable medical device, can be based on the previous program version. If the operation of the implantable medical device later encounters errors, the restore point of the previous program can be loaded in place of whichever later program version is inappropriately running. However, a check might automatically be performed by the implantable medical device to determine whether the previous program version is associated with a drug that is no longer within the implantable medical device, while other compatibility checks might additionally or alternatively be performed. Delivery of a different and/or stronger drug at the delivery rate settings associated with the weaker drug risks overdosing the patient, and delivery of a different and even far weaker drug at the delivery rate settings associated with the weaker drug risks underdosing the patient. As such, the restoration to the restore point might only take place if the automatic check determines that the fluid (containing a drug) currently within the implantable medical device and available for delivery is the same or similar fluid associated with the restore point. Different compatibility checks may be performed depending on the application. By being able to account for compatibility between a restore point and a device state, a programmer and/or device can automatically make decisions about whether enactment of a previous program version would be beneficial or harmful.

In some embodiments, the programming of an implantable medical device can revert to a restore point based on inadequate therapy results. It can be preferable in some cases to run a previous therapy regimen in an implantable medical device as compared to a newer therapy regimen that is ineffective or associated with malfunction of implantable medical device. The later program version might be associated with experimental therapy settings, for example. The programming reversion of the implantable medical device by loading a restore point may not be based on a programming error, but rather on dissatisfaction with the efficacy or side-effects of a newer therapy and a preference for an older therapy for which the implantable medical device is still capable of delivering. While a patient and/or clinician may initially desire to restore old settings by loading the program instructions of a previously used program version, the patient and/or clinician may be unaware or have forgotten that the previous therapy delivery settings of the previously used program version are inappropriate for a current device state. Control circuitry functioning as described herein can evaluate whether a roll back to a previous program version by loading a restore point would result in running older delivery parameters that could potentially harm the patient by mismatching a therapy settings (e.g., a high fluid delivery rate setting meant for a weaker drug) with a current state of the device (e.g., a strong drug in the reservoir intended for a low rate of fluid delivery), among other checks.

FIG. 1 illustrates a flow chart of a method 100 for reverting operational programming of an implantable medical device. The method 100 includes programming 110 the implantable medical device with a first program version. In some cases, the first program version of the programming 110 can be referred to as a previous program version, an initial program version, or a prior program version. The method 100 further includes reprogramming 120 the implantable medical device to operate using a second program version. The second program version can also be referred to as an updated program version, a latter program version, or a subsequent program version, as this second program version replaces a program version previously programmed 110 into the implantable medical device. In this way, reprogramming 120 can displace the first program version being run on the implantable medical device to control some or all of the functions of the implantable medical device with a second program version.

A program version, as used to herein, refers to a set of logical instructions that can be loaded on an implantable medical device and executed by processing circuitry to govern operation of the implantable medical device. A particular program version may not govern all functions of an implantable medical device (e.g., a particular hardware component may have its own dedicated logic). However, in typical embodiments, the program version is central to the operation of the implantable medical device such that the implantable medical device is only able to run one program version at a time, whereas running another program version would require rebooting of the implantable medical device. In some embodiments, the program version of an implantable medical device is the firmware of the implantable medical device. As will be discussed further herein, multiple program versions can be saved in an implantable medical device (e.g., as multiple restore points), however only one particular version can be run at a time.

It is noted that reference herein to a first program version and a second program version is not intended to imply that the first program version was the original program version programmed into the implantable medical device before any other program version, and/or that the second program version immediately followed the first program version without an intervening program version. Rather, reference to first and second program versions refers to the relative order between the program versions (i.e. that the first program version was used before the second program version as the current program version). Reference herein to a first program version and a second program version does not preclude an understanding whereby a different program version was used as a current program version between use of the first and second program versions and/or that other program versions were used by the implantable medical device before and/or after the first and second program versions were used by the implantable medical device.

Returning to the flowchart of FIG. 1, the method 100 further includes determining 130 determining whether the implantable medical device will be able to operate using the first program version to deliver therapy according to the first program version if the implantable medical device was to revert back to using the first program version. For example, it can be determined 130 whether the implantable medical device is still equipped to implement a previous program version with which the implantable medical device was programmed 110 following the implantable medical device being reprogrammed 120 with an updated program version, where the initial programming 110 and then reprogramming 120 may be separated by hours, days, months, or years, and over such time the state of the implantable medical device may have changed by depletion (e.g. drug in reservoir, battery power), in function (e.g. a lead or other component may be malfunctioning, or no longer authorized to be used), in programming (e.g., the implantable medical device operates according to at least some updated program instruction), and/or in setup (e.g., a lead swapped or a drug changed), among other possible changes in configuration.

The determining 130 step may be performed by an external programmer that has performed one or both of the programming 110 and reprogramming 120 steps, however not all options are so limited. The determining 130 step may be performed during a programming session between the external programmer and the implantable medical device. For example, the reprogramming 120 and determining 130 steps may be performed at the same time or a least during the same programming session with an external programmer. In some cases, determining 130 may be performed shortly after reprogramming 120 during the same telemetry session. The external programmer may be updating the program version of the implantable medical device in the reprogramming 120 step while also determining 130 whether the program version being replaced is compatible with other changes to the implantable medical device that might be taking place. These changes might include the physical changing of a drug, a catheter, or a lead, and/or enabling or disabling particular therapy capabilities, among other things. Changes may additionally or alternatively relate to the program version itself, such as a change of a drug delivery parameter (e.g., fluid rate) and/or an electrode configuration (e.g., a different electrode combination selected for stimulation). In the cases where the reprogramming step 120 and the determining 130 step are performed in the same programming session, and the determining 130 step concludes that appropriate compatibility does exist between the current or future state of the implantable medical device (as changed) and the first program version with which the implantable medical device was previously programmed 110, then the implantable medical device may be further programmed with a restore point corresponding to the first program version with which the implantable medical device was previously programmed 110. The restore point can be saved in memory of the implantable medical device while the second program version is used to control operation of the implantable medical device. If the implantable medical device encounters an error or a particular external command is received, then the implantable medical device can load the restore point by reverting 140 operational programming of the implantable medical device from the second program version to the first program version, whereby the first program version displaces the second program version in controlling the operation of the implantable medical device.

In some cases, the changes relate to programming of the implantable medical device, such as firmware or programming at the application level. Incompatibilities between different components of a program version could be detected, and the current programming of an implantable medical device may mean it will not be able to operate using a prior (first) program version to deliver therapy. For example, a first firmware version may expect fluid rate schedule information (or other therapy output parameters) to be encoded one way (e.g. as a list of 36 tuples of constant rate, duration, and what tuple to run next) and a second firmware version may expect the fluid rate schedule information to be encoded differently than the first firmware version (e.g. with coefficients a, b, and c of an equation $a*t^2+b*t+c$ provided instead of constant rate values; where t is time since the start of the period and thus allowing a series of linear, curved and/or constant rates to be defined instead of just a series of constant rates). If the implantable medical device is programmed with the first firmware version and an appropriate fluid rate schedule information, and is then reprogrammed with the second firmware version and the coefficients and time values appropriate for the second firmware version, it might be determined 130 that the implantable medical device would not be able to operate using the first firmware version in a reversion to the first firmware version if either the appropriate fluid rate schedule information is no longer available or a safe transition could not be made from the variable therapy of coefficients and time values back to the constant fluid rate schedule information. As discussed herein, some transitions between therapy delivery protocols will not be allowed (e.g., by not creating a restore point or by not reverting to a restore point) because of the risk posed to a patient by a sudden change in therapy level.

Although the above discussion presents some options where the external programmer partially or wholly performed the determination 130 during a programming or telemetry session with the implantable medical device and then programmed the implantable medical device with the ability to perform the reversion 140 at a later time, in some embodiments the implantable medical device performs the determination 130 during the session or at a later time. For example, one or more restore points may be saved on the implantable medical device based on one or more rounds of programming 110 and reprogramming 120 (e.g., each reprogramming 120 producing another restore point based on whichever program version is being replaced). If the implantable medical device then later encounters an error or a particular external command is received, then the implantable medical device can evaluate the one or more restore points to see whether any of them are compatible with a current state of the implantable medical device, which can include determining 130 whether the implantable medical device will be able to operate using the first program version to deliver therapy according to the first program version if the implantable medical device was to revert back to using the first program version. If the implantable medical device is equipped to implement therapy consistent with one of the program versions of one of the restore points, then the implantable medical device can implement that restore point by reverting 140 operational programming of the implantable medical device from the updated (i.e. second, later, or otherwise current) program version to the program version of the restore point (e.g., first, initial, or otherwise previous program version). As such, the determination 130 step can be done at different times, such as at a time of reprogramming 120, at a time when the implantable medical device would otherwise be relatively idle, and/or as a problematic condition develops. The ability to perform the determination 130 step at different times allows the implantable medical device to flexibly adapt to different changes within the implantable medical device, such as depletion of drug in a reservoir, disablement of particular features, accommodating therapy changes, and accommodating hardware or programming failures on the implantable medical device. Changes can also include changes to the environment of the implantable medical device, changes in positioning (e.g., position of a catheter or electrode), and/or changes in patient state. For example, a patient may be undergoing a seizure and such a patient state may prohibit a reversion 140 to a prior program version. In such a case, an implantable medical device may wait until the seizure or other condition has changed before reversion 140.

It is noted that the reprogramming 120 step may be performed multiple times to possibly set multiple restore points. One of the multiple restore points may later be used for reversion 140 of operational programming if the implantable medical device is determined 130 to be able to implement therapy consistent with the program version of the one restore point. The program version of the one restore point out of the multiple restore points that replaces the current program version in the reversion 140 may not necessarily be the program version that the current program version previously replaced in reprogramming 120, as the implantable medical device may have serially used multiple intervening program versions over time.

Restoration of a previous program version by reversion 140 can allow the implantable medical device to sidestep problematic issues that may have developed over time by using a program version that was previously used in the implantable medical device. This approach can automatically handle errors that might otherwise compromise therapy delivery. In some conventional approaches to handling error, a patient might be alerted of the error (e.g., via the patient programmer) and/or the patient may notice the lack of efficacious therapy. The patient may then have to schedule a visit with a clinician to address the problem. This might be particularly inconvenient for patients that live long distances from their clinician (e.g., a patient in a rural area might live hundreds of miles from his or her specialist doctor in another state or country), and might have to arrange a flight or other transportation just to get evaluated. Returning to the clinician may be especially inconvenient if a recent reprogramming 120 session introduced the error and the patient traveled home only to realize the error. The opportunity to restore a previous program version can at least temporarily allow therapy to continue until the patient is evaluated or the previous program version could be relied upon to provide therapy for extended periods until the next scheduled appointment with a clinician. Also, in contrast to devices that implement basic default therapy setting that might not have ever been tried on the patient when an error is encountered, various embodiments of the present disclosure attempt to restore a program version of the device that was fully functional and, for at least a time, implemented therapy selected for the particular patient.

Figure 2:
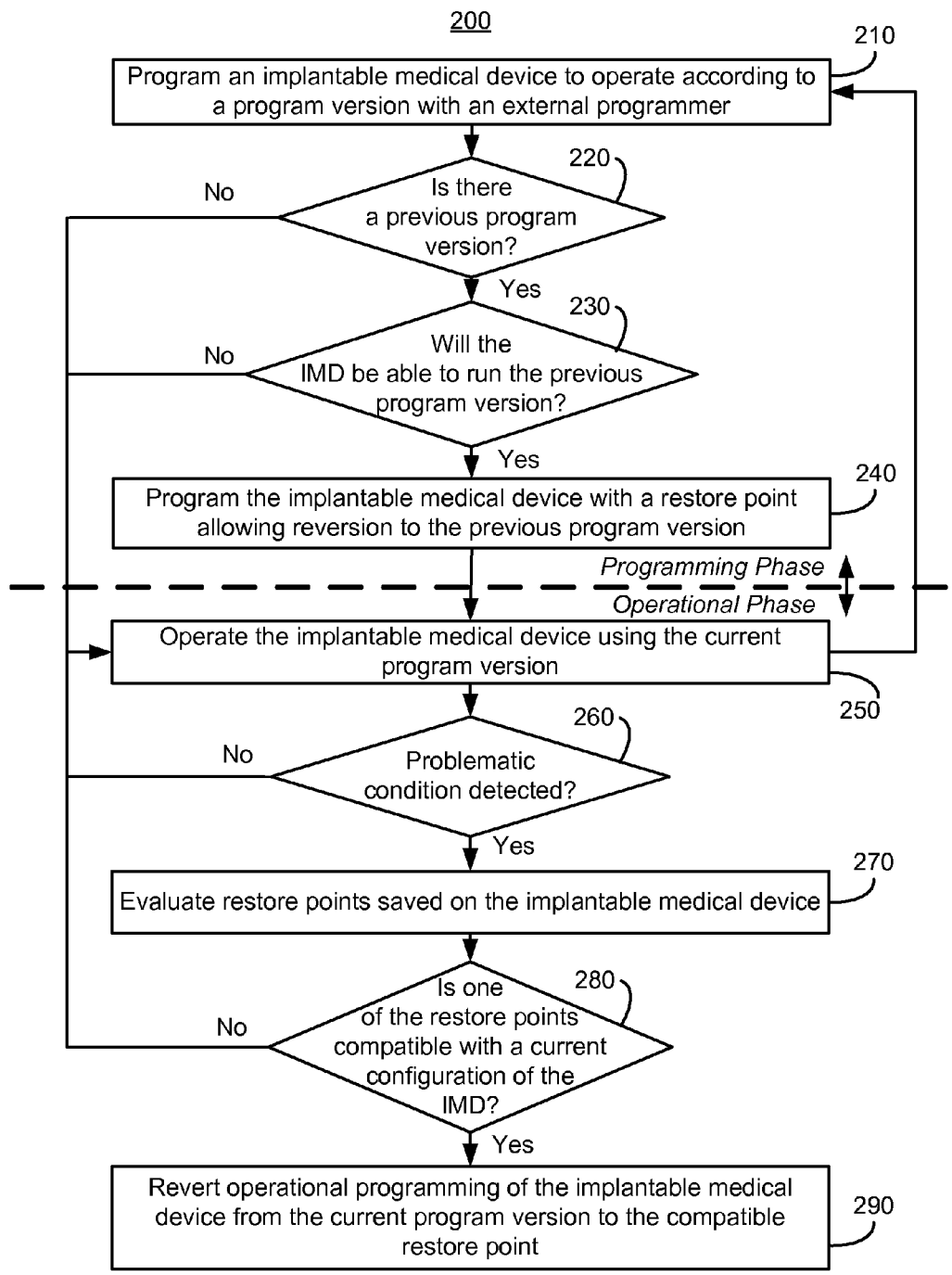
FIG. 2 is another flowchart of a method according to various embodiments for restoring programming in a medical device.

FIG. 2 illustrates a flowchart of a method 200 for saving one or more restore points on an implantable medical device and enacting one of the restore points based on a problematic condition. The method 200 of FIG. 2 may concern some of the same embodiments as the method 100 of FIG. 1 (or any other embodiment referenced herein), with the different flowcharts highlighting different aspects of the various embodiments.

The method 200 includes programming 210 an implantable medical device to operate according to a program version with an external programmer. Programming 210 may include programming the implantable medical device with a first program version. The programming 210 step may be performed for the first time for a particular implantable medical device in a factory or clinic, and in such a case there might not be a previous program version saved on the implantable medical device. Check 220 may determine whether a program version was already loaded on the implantable medical device to actively control the operation of the implantable medical device before the updated program version of the programming 210 step is used by the implantable medical device. If no previous program version was being used to control operation of the implantable medical device according to check 220, then the implantable medical device can operate 250 according to the program version with which the implantable medical device was just programmed 210, which might include delivering a therapy, monitoring, and/or performing some other function in an operational phase. In this example, no previous program version is available upon which to base a restore point because the implantable medical device has only been, or will only be, loaded with one program version as part of programming 210.

If, however, the check 220 determines that a previous program version was being run or otherwise did actively exist on the implantable medical device at the beginning of programming 210 (or that a program version does currently exist but will be replaced by the end of the current programming 210), then check 230 can be performed to determine whether the implantable medical device will be able to operate using the previous program version (i.e. the program version being replaced by programming 210) to deliver therapy according to the previous program version if the implantable medical device was to revert back to using the previous program version following programming 210. It can understood that the programming 210 step is replacing a first program version with a second program version in controlling the operation of the implantable medical device and that the check 230 is evaluating whether the implantable medical device will be able to operate using the first program version to deliver therapy according to the first program version if the implantable medical device was to revert back to using the first program version following the programming 210 that replaced the first program version with the second program version. It can be understood that the programming 210 step can be deemed a reprogramming step when it replaces one program version (e.g., a first program version) with another program version (e.g., a second program version).

Check 230 may be performed, in some embodiments, because some changes in an implantable medical device over time could render the implantable medical device unable to safely or effectively run a previous program version. For example, the type of drug within an implantable drug pump may be changed, or the concentration of the drug may be changed, where using the delivery protocol of a prior program version with a different drug or drug concentration could risk underdosing or overdosing a patient, which can have fatal results depending on the drug and the medical issues the drug is addressing. Other changes to an implantable medical device could include changing a catheter for drug delivery which may have a different length or lumen size which can alter drug delivery rates, changing a lead which may have a different electrode configuration, disablement of electrodes (e.g., a clinician may disable the use of an electrode that is associated with unwanted stimulation), or changing some other aspect of an implantable medical device that might render the implantable medical device unable to successfully operate using a previous program version that was previously used by the implantable medical device before the change. Other changes that can prevent reversion to a particular program version may include changes in the location of one or more delivery components (e.g., catheter or electrode), a component of the device reaching an end-of-service life, changes in operational logic and/or therapy setting programming, program instructions associated with a recall, and/or flagged settings (e.g., by a clinician, an update, or a factory setting indicating that particular programs or settings should only be used with caution or never used). Other changes include a detection of the memory storing the previous program version to be bad/corrupt and unrecoverable or if a "terminal event" error condition occurs such that the device is considered unfit for operation regardless of the program version.

In some cases, an evaluation may be performed to determine whether reversion may be inappropriate based on therapy parameters and/or clinical factors. For example, if a previous program version is associated with a different clinician and/or clinic, an automatic reversion may not be allowed to the previous program version (e.g., unless the reversion is specifically authorized by the current clinician and/or clinic). In some cases, reversion is not allowed if such a reversion would enact an asynchronous rate therapy event, such as a one-time event. In some embodiments, an evaluation can be performed to determine whether the reversion would change the therapy output by a predetermined amount, and a reversion would not be automatically performed if the reversion would change the therapy output more than the predetermined amount. For example, a threshold can be set at 25% (or some other amount), and the evaluation could evaluate the current level of therapy and the level of therapy of the prior program version under consideration (e.g., evaluating the drug delivery rate or stimulation voltage), and an automatic reversion may only be allowed if there is less than a 25% difference of the therapy levels.

In some embodiments, the changing of therapy delivery parameters, where the change in the therapy parameters is determined to be critical, could mean that reversion to previous therapy parameters used before the change could endanger the patient. In such cases, an implantable medical device can be contra-indicated from using therapy parameters that overlap with previous therapy parameters of a restore point. For instance, a change in therapy parameter limits (e.g., by way of programming 210) can render therapy parameters of a previous program version outside of the new limits. It would therefore be inappropriate to revert to this previous program version. However, if the implantable medical device can revert back to a previous program version while keeping within new therapy delivery parameter limits, then in such a case, the check 230 may determine that the implantable medical device is able to operate using the previous program version of the restore point to deliver therapy according to the program version on which the restore point is based if the implantable medical device was to revert back to using the program version.

If the check 230 determines that the implantable medical device will be able to operate using the program version (e.g., the first program version) being replaced by programming 210 (e.g., adding the second program version) to deliver therapy according to the program version if the implantable medical device was to revert back to using the program version, then the implantable medical device can further be programmed 240 by the external programmer with a restore point that allows the implantable medical device to revert to the program version being replaced by programming 210 under certain conditions. If the check 230 determines that the implantable medical device will not be able to operate using the program version being replaced by programming 210 to deliver therapy according to the program version being replaced, then the implantable medical device will not set a restore point based on the program version being replaced by programming 210, and will then operate 250 the implantable medical device using the program version currently being added in the programming 210 session.

Programming 240 the implantable medical device with a restore point can be performed in various ways. In some embodiments, an external programmer performs the programming 240. In some cases, the implantable medical device can perform the checks 220 and 230 and program 240 itself with the restore point. Programming 240 the implantable medical device with a restore point can include saving a full version of the previous program version, only the essential parts of the previous program version to run therapy, or only the parts of the previous program version that differ from another program version (e.g., the current program version being run). The restore point may be saved in the memory of the implantable medical device along with the current program version, in a partitioned area of memory separate from the current program version, or in a different memory structure altogether separate from the memory structure containing the current program version.

Programming 240 the restore point can include saving program instructions in memory of the implantable medical device that are not loaded or executed while the implantable medical device runs or otherwise operates according to a current program version, but may be accessed and loaded to displaced a current program version to control the function of the implantable medical device in accordance with the prior program version on which the restore point is based. The saved program instructions could be the same program instructions previously used by the implantable medical device to operate according to the prior program version. In some embodiments, the saved program instructions may be similar, but not identical, to the program instructions previously used by the implantable medical device to operate according to the prior program version, wherein the program instructions have been changed to account for the program instructions being packaged as a restore point and not the standard operating program version. The saved program instructions of a restore point can be saved in memory in the same format for which they can be used by the processing circuitry if restoration is needed. In some embodiments the saved program instructions of a restore point can be in a compressed and/or encrypted state while stored in the memory, where decompression or decryption is needed if the restore point is to be used (e.g., loaded in RAM and used to operate the implantable medical device). Compression can save space in memory of the implantable medical device, which might be particularly important for program instructions that, under best case scenarios, will not be used.

It is noted that the programming 210 step of FIG. 2 can correspond to each of the programming 110 and reprogramming 120 steps of FIG. 1 because a loop in FIG. 2, branching from the operation 250 step, can allow the method 200 to repeatedly return to the operate 210 step for reprogramming.

The method 200 of FIG. 2 comprises a programming phase and an operation phase. Once the programming 210 of the current program version and optionally the programming 240 of the restore point are complete as part of the programming phase, the implantable medical device can operate 250 using the current program version in the operational phase. The operating 250 step refers to the primary function(s) of the implantable medical device, such as delivering therapy and/or monitoring, depending on the application. It is expected that an implantable medical device will spend most of its implanted life in the operational phase, specifically operating 250 using the current program version, and not using the program instructions particular to a restore point. However, errors or other problems may cause the implantable medical device to use the program version of a restore point instead of the current program version, as discussed further herein.

In the operational phase, a check 260 is periodically performed to determine whether a problematic condition is detected. The check 260 may include determining whether any routines have timed out, whether all components are responding appropriately, whether intended functions are being carried out (e.g., that stimulation or fluid is in fact being delivered), that all integrity and diagnostic checks of hardware and other components are satisfied, that check sums are correct (or other technique for testing whether sections of memory are corrupted), and/or any other technique for identifying whether an implantable medical device is malfunctioning in some manner.

In some embodiments, an error, a timeout of a routine, a failure to detect any physiological events, detection of physiological events at an unrealistic rate, and/or another indicator of malfunction can cause an implantable medical device to reboot or otherwise reset. A reset can clear currently running or pending routines and reload the program instructions of the current program version of the implantable medical device. A reset may be successful in addressing some malfunctions, particularly minor and rare malfunctions that are unlikely to occur again. However, if a threshold number of resets occur within a certain amount of time (e.g., 4 resets within a day), as determined by a reset counter, then the check 260 can confirm detection of a problematic condition. Use of a reset counter threshold before restoration allows an implantable medical device several attempts to resolve problems while maintaining the current program version before switching program versions via loading a restore point. As such, not all error conditions are appropriate for restoring a previous program version, and the check 260 can attempt to decide whether the patient would be better off with the current program version (with errors) or with a prior program version (which hopefully lacks errors but may not function in the same manner as the current program version that it would replace).

In some cases, a need for reversion to a restore point can be triggered by the occurrence of a race condition where differences in timing of events lead to an intermittent issue. Other conditions include improper use or management of memory.

In various embodiments, a problematic or unexpected condition can be detected by a watchdog feature. A watchdog feature may communicate with a processor running firmware of the implantable medical device (e.g., as the program version), the watchdog feature expecting a report from the processor indicating proper function at periodic intervals. If the indication is not received for one or some threshold number of intervals, then it can be assumed that an error is present preventing proper function of implantable medical device in running the current program version (e.g., a time-out or non-responsive condition). A watchdog feature may increment an error count and/or reboot the implantable medical device. A predetermined number of error counts and/or reboots may cause the problematic condition to be detected thereby passing check 260, initiating consideration of reversion to a restore point as in the evaluation 270 step.

Depending on the embodiment, error detection may comprise, without limitation, determining if too little or too much time has passed between commands, evaluating sequence numbering, comparing therapy parameter values to device and/or patient specific acceptable ranges, comparing dosage values set forth by the programming instructions to labeling instructions for a medication, identifying a mismatch of commands (e.g., stimulation instructions for a drug delivery device), recognizing an invalid pattern of commands or command data (e.g., a repeated loop), identifying contradictions to previous commands (e.g., drug reservoir is empty after refilling drug reservoir), and/or any number of other checks.

As long as the check 260 does not detect a problematic condition, then the method 200 continues with operation 250 of the implantable medical device. However, if the check 260 detects a problematic condition that may justify switching program versions, then the implantable medical device evaluates 270 some or all of the restore points saved on the implantable medical device. Evaluation 270 can include performing one or more checks to determine whether a current configuration of the implantable medical device is compatible with the respective operations of the program versions of the restore points.

A compatibility check of the evaluation 270 can include determining whether all the necessary hardware to implement a previous program version of a restore point is still operational and/or enabled. For example, a particular electrode combination may have been identified as being associated with an unwanted side effect or a manual or automatic diagnostic check may have determined that a lead or electrode is inoperable (e.g., an impedance check identified a break in a conductor of a lead). In these cases, if a restore point would run a previous program version that requires a component that is now not operational, then that restore point can be identified to not be an option for restoration in the evaluation 270.

Further checks of the evaluation 270 can include determining whether a drug has been depleted from a reservoir, whether the drug has expired, and/or whether the drug has been changed (e.g., type or concentration). For example, if the drug of a previous program version of a restore point being evaluated 270 has been depleted such that it cannot be delivered by a pump, then the check 280 could determine that the restore points are not compatible with the current configuration of the implantable device.

In some embodiments, one or more restore points may concern operating the implantable medical device according to a closed loop algorithm. In such cases, evaluation 270 may determine whether the input to the closed loop algorithm is available to be used for closed loop control. For example, an algorithm for deep brain stimulation may be based on a sensed brain signal. Evaluation 270 may vet a restore point by determining whether the implantable medical device can accurately sense the brain signal, where malfunctioning sensing circuitry, lack of a properly positioned sensor (e.g. due to lead migration), high environmental noise, and/or an inability to discriminate a biomarker in a signal, among other things, may cause the restore point to fail check 280. In this way, the state of the implantable medical device may change such that a previous program version could not be properly run if the implantable medical device loaded the previous program version to replace a current program version that is malfunctioning.

Evaluation 270 can check all restore points saved on the implantable medical device for compatibility with a current state of the implantable medical device, which might be one, two, three, ten, or some other number of restore points, which are all associated with different program versions previously used on the implantable medical device and different ways of operating the implantable medical device.

Check 280 can be performed to determine whether the implantable medical device will be able to operate using a previous program version of a restore point to deliver therapy according to the previous program version if the implantable medical device were to replace the current program version by reverting back to using the previous program version based on the evaluation 270. While the check 280 in the flowchart specifically mentions compatibility, check 280 may also be performed on additional or alternative bases, such as whether the therapy parameters of a restore point would not be any more probable than the current therapy parameters to harm the patient or produce an unacceptable side effect.

In another example, system power considerations may determine whether a reversion to a previous program version is possible. For instance, if power levels of a prime-cell or rechargeable power source of an implantable medical device have been depleted below a certain threshold since the creation of the restore point associated with the previous version, and if the previous version involves therapy delivery that requires larger amounts of power that are no longer considered available from the power source, it may be determined that reverting to this previous version is not allowable.

If the check 280 recognizes that none of the restore points saved on the implantable medical device are compatible with the current configuration of the implantable medical device according to the evaluation 250, then the implantable medical device can continue to operate 250 using the current program version. In this case, an error message may be produced (e.g., vibrating and/or beeping of the implantable medical device) to alert the patient or clinician of the problem with the current program version and the inability for the implantable medical device to resolve the problem. If, however, the check 280 recognizes that one of the restore points saved on the implantable medical device is compatible with the current configuration of the implantable medical device according to the evaluation 270, then the implantable medical device can revert 290 operational programming from the current program version to the compatible restore point (i.e. the program instructions of the restore point, previously used as a prior program version, can again be used to control the functions of the implantable medical device). In this case as well, an alert may be provided to the patient and/or clinician upon reversion 290. In some cases, the alert may contain information regarding the nature of the error that triggered the reversion, routines leading up to the reversion, information about the reversion version selected for use, and/or conditions leading up to the reversion.

The flowchart of FIG. 2 demonstrates multiple areas where control circuitry of one or both of an implantable medical device and an external programmer (e.g., respective processors and memory running in coordination in each of the implantable medical device and the external programmer) can automatically address problematic conditions. In particular, the flowchart of FIG. 2 shows two steps that automatically determine whether previous program versions (check 230 and check 280) would be appropriate for restoring. Specifically, check 230 determines whether a restore point should be made based on a previous program version and check 280 determines whether the restore point should actually be used. In various embodiments, only one of these checks may be made by control circuitry. For example, a clinician may evaluate previous program versions and exercise control over whether each is saved on an implantable medical device, erasing or invalidating those deemed inappropriate for reversion. In these cases, check 230 may not be performed by control circuitry but evaluation 270 and check 280 may be performed in the operational phase by control circuitry of the implantable medical device once a problematic condition has been detected. In some cases, the check 230 is performed automatically but a confirmation is required from clinician via an external programmer before the implantable medical device is programmed 240 with a restore point.

In some embodiments, an external programmer and/or implantable medical device will only allow a single restore point to be saved on the implantable medical device, and in such cases the implantable medical device may simplify the evaluation 270 and the check 280 because only one restore point will need to be evaluated. Alternatively, the implantable medical device may automatically revert 290 to the single saved restore point upon detection of the problematic condition by check 260 without evaluating 270 or checking 280 the restore point. In such cases, the check 230 performed during programming can provide assurance that the device will be able to implement the single restore point during the operational phase if necessary. Such embodiments are better suited to situations whether the state of the implantable medical device is unlikely to change between the programming 210 session and some later time in the operational phase.

In some cases, restore points are programmed 240 into the implantable medical device without performing check 230. In these cases, evaluation 270 and check 280 by the implantable medical device are used to provide assurance that restoration 290 to a restore point is an appropriate course of action. In view of these and other options, it will be understood that FIG. 2 illustrates one embodiment and that modifications of the method 200 are within the scope of this disclosure, including adding and/or omitting one or more steps of the illustrated embodiment.

It is noted that either or both of the checks 230 and 280, concerning determining whether the implantable medical device will be able to operate using a previous program version, can correspond to determining 130 step of FIG. 1 that determines whether the implantable medical device will be able to operate using a first program version to deliver therapy according to the first program version if the implantable medical device was to revert back to using the first program version.

It is noted that the method 200 of FIG. 2, as well as various other embodiments of this disclosure, can create multiple restore points over the course of multiple programming sessions. Furthermore, multiple restore points may be saved on an implantable medical device when a problematic condition necessitates evaluation and reversion to one of the restore points. Only one program version can be run on an implantable medical device at a time, so an implantable medical device may be configured to evaluate the restore points and select between them. The selection may prioritize the most recently saved restore point, the oldest restore point, the restore point based on the previous program version that is most similar to the current program version, or the restore point based on the previous program version that is most dissimilar to the current program version, and select the prioritized restore point for reversion over other restore points. Such an evaluation may only be performed on the restore points that have already passed other filters, such as the check 280 of FIG. 2 or other checks of other embodiments herein.

Figure 3:
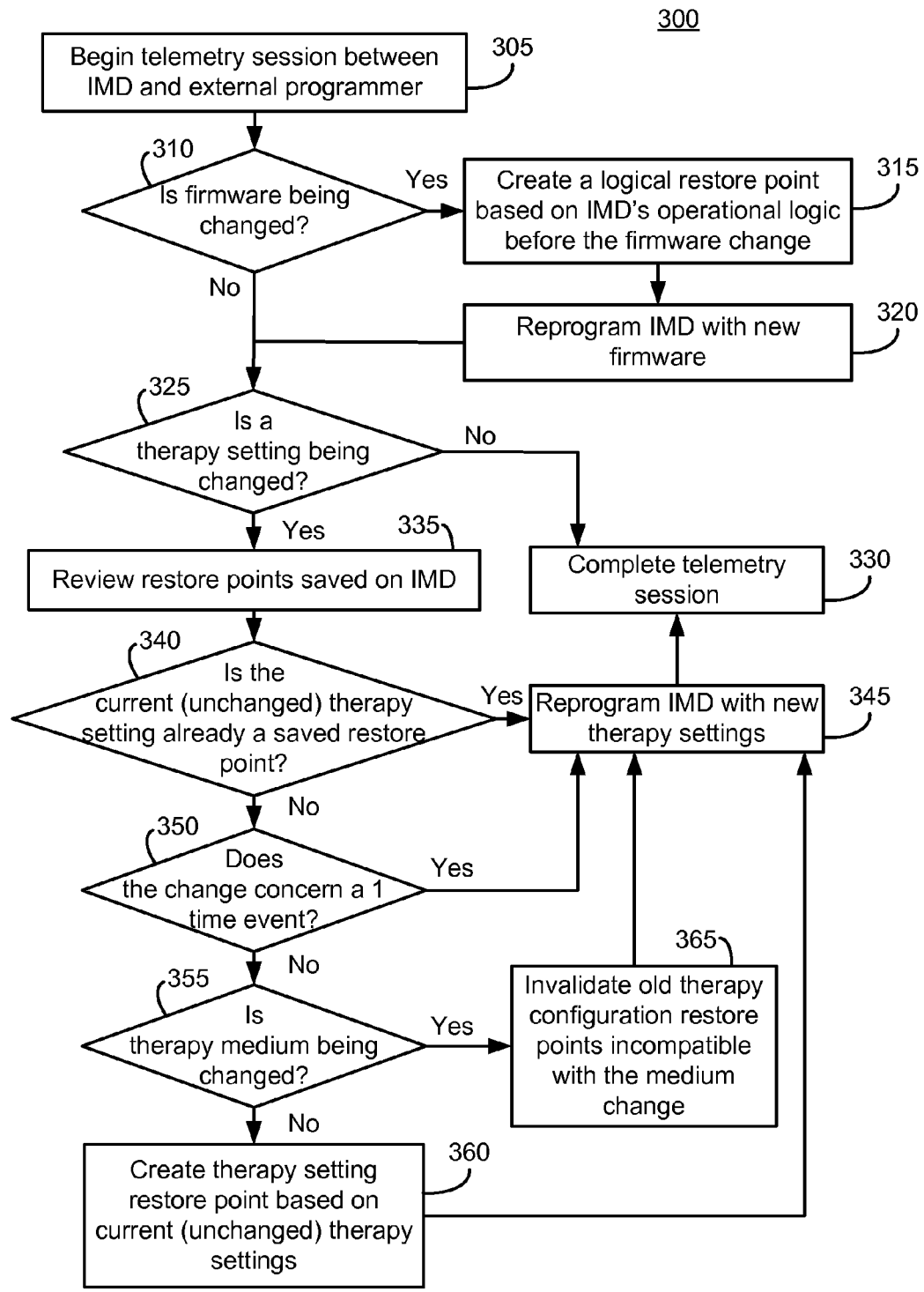
FIG. 3 is a flowchart of a method according to various embodiments for programming a medical device with a restore point.

FIG. 3 is a flowchart of a method 300 for programming an implantable medical device with one or more restore points. The method 300 can concern the same embodiments as FIGS. 1 and 2 while highlighting different aspects and options. In particular, the method 300 of FIG. 3 can correspond to the programming phase of the flowchart of FIG. 2. As will further be detailed, the flowchart of FIG. 4 can correspond to the operational phase of FIG. 2.

It is noted that the flowchart of FIG. 3 separates each program version into two components. The first component is firmware, which refers to the program instructions that control the most basic functions of the implantable medical device, which may or may not include therapy delivery functions. Functions that can be controlled by firmware include time keeping (e.g. number of minutes since battery connect), updating therapy delivery based on timing, periodic diagnostic checks (e.g., stall detection algorithms, safety interlock checks), alerts, telemetry support, power supply monitoring and reporting, recharge control (in the event the power source is rechargeable), event logging, and/or analyzing sensed data. The second component of each program version comprises therapy settings, which concern the parameters that an implantable medical device can use for therapy delivery (e.g., pulse amplitude, fluid volume delivery rate). Separating a program version into these two components can have particular troubleshooting advantages, as will be demonstrated in FIGS. 3 and 4.

The flowchart of the method 300 of FIG. 3 starts with the beginning 305 of a telemetry session between an implantable medical device and an external programmer. Transcutaneous telemetry between an implanted medical device and an external programmer can be carried out by any technique disclosed herein or known, such as, for example, wireless communication via inductance and/or radio frequencies using one or more protocols between the external programmer and the implanted medical device.

During the telemetry session, a check 310 can be performed to determine whether firmware is being changed as part of the session. Either of the implantable medical device and/or the external programmer may determine whether firmware of the implantable medical device is being changed in the session, such as by monitoring for commands that change the firmware of the implantable medical device. If the check 310 determines that the firmware of the implantable medical device is being changed, then the method 300 can create 315 a logical restore point based on the implantable medical device current operational logic in place before the firmware change. In this way, a restore point can be created 315 and saved in the implantable medical device based on the firmware program version that was controlling operation of the implantable medical device at the beginning 305 of the programming session. The implantable medical device can then be reprogrammed 320 with the new firmware such that the implantable medical device will operate according to the new firmware, unless a restoration of the prior firmware program version is needed as further discussed herein.

A logical firmware restore point can later be loaded to replace a newer set of firmware instructions according to which the implantable medical device actively operates with older firmware instructions of a previous program version. In some embodiments, the replacement of firmware program instructions can change some basic functions of the implantable medical device without changing therapy settings, such as power management and telemetry.

Following reprogramming 320 of the implantable medical device with new firmware, or if no firmware change was identified in check 310, the method 300 can continue with the telemetry session to check 325 to determine whether a therapy setting is being changed in the telemetry session. Therapy setting change check 325 can be performed by one or both of the implantable medical device and the external programmer, and can include determining whether any changes are being made to the therapy settings of the current program version as part of the telemetry session. In various embodiments, changes to therapy settings can include, but are not necessarily limited to, increases or decreases to stimulation parameters (e.g., voltage, amplitude, pulse width, frequency), drug delivery parameters (e.g., rate of delivery, amount of delivery in a bolus, bolus limits for patient initiated delivery), changes to closed loop settings (e.g., lowering or raising a threshold for triggering therapy), and/or changes to delivery schedules. In various embodiments, therapy setting change check 325 concerns the parameters that primarily will be used to deliver therapy following the telemetry session as part of a current program version, such as the stimulation parameters for a neurostimulator or the drug delivery settings for an implantable drug pump.

Although not illustrated in the flowchart of FIG. 3, some embodiments of this disclosure can evaluate whether previously used program settings were satisfactory. If therapy settings are being changed according to check 325, control circuitry can evaluate whether the therapy settings being replaced function within an acceptable margin. For example, a sensed parameter of a patient state may indicate an acceptable patient condition, indicating that the therapy parameters managed the condition to an acceptable level. Additionally or alternatively, a query may appear on a display of the external programmer asking the patient or clinician whether the therapy settings being replaced were acceptable. If it is determined that the therapy settings being replaced were not acceptable, then the method 300 would not create a restore point based on the therapy settings being replaced. However, if the determination did indicate that the therapy settings were acceptable, then the method 300 can continue with creating a therapy setting restore point. Although the above discussion used therapy settings as an example, various embodiments could apply the same concept to program versions generally, where a restore point is only created if the program version on which it is based receives an indication of approval (or lack of disapproval) from a patient or clinician or is evaluated to function acceptably by control circuitry (e.g., did not produce any errors when previously run).

If the therapy setting change check 325 determines that no therapy changes are being made in the telemetry session, then the method 300 can complete 330 the telemetry session (or at least exit the routine of FIG. 3). Completing 330 the telemetry session can refer to ending the telemetry session or carrying out other tasks of the telemetry session (e.g., uploading data sensed by the implantable medical device).

If the therapy setting change check 325 determines that therapy changes are being made in the telemetry session, then the restore points already saved on the implantable medical device can be reviewed 335. Review 335 can analyze, among other things, the current (but being replaced) therapy settings and the therapy settings of all of the stored restore points. If the current (but being replaced) therapy settings are already present in another restore point saved on the implantable medical device, according to check 340, then the implantable medical device can be programmed 345 with the new therapy settings without setting a new restore point for the therapy settings being changed. In this situation, it is unnecessary to create multiple restore points corresponding to the same therapy settings when only one may be needed if a roll back of therapy settings is needed.

If check 340 determines that the current (but being replaced) therapy settings are unique compared to the already saved restore points, then the method 300 can continue trying to automatically determine whether the creation of a restore point is appropriate. In such a case, the method 300 can determine 350 whether the change concerns a one-time event. Check 350 may be useful because some changes to therapy settings in various embodiments merely reprogram the implantable medical device for a one-time event. For example, a patient may have a medical procedure scheduled (e.g., surgery) and the therapy parameters may need to be turned up (e.g., if the therapy alleviates pain) or down (e.g., if the therapy might interfere with the surgery) temporarily. In some cases the one-time event may concern a trip that the patient is going to be taking or other activity in which the patient seldom engages, and therapy settings are being customized for the trip or activity in the telemetry session. In some cases, the one-time event may concern bridging from an old to a new drug, priming after aspiration or connection of a different catheter, or other aspects of therapy delivery and temporary delivery settings are needed to accomplish the change. In any case, different options can be taken if the change is identified to concern a one-time or seldom-occurring event by check 350.

In some embodiments, a restore point that might revert operation of the implantable medical device back to the therapy settings of the one-time event will not be generated. For example, it might be undesirable if an implantable drug pump reverts back to a delivery parameters meant for priming which might be performed at the highest delivery rate and could risk delivering too much of a drug to the patient. In some embodiments, it is assumed that therapy settings to be used after the one-time event are also being programmed into the implantable medical device, and in which case it might be preferable to wait for those settings to be enacted than to attempt a restoration to a previous therapy setting which might risk repeating or prematurely truncating the one-time event. In these cases, it can be preferable to not generate a restore point corresponding to the one-time event or for a therapy setting used before the one-time event. As shown in the flowchart, if the therapy setting change concerns a one-time event, then implantable medical device is reprogrammed 345 without adding a therapy setting restore point. In some cases, a restore point can be set based on a therapy setting with one-time event information stripped out. For example, a therapy setting can include an initial pump clearing or other routine (as the one-time event) and then a particular fluid delivery rate. A restore point based on this therapy setting may include the fluid delivery rate but may omit commands for the pump clearing. The restore point may further include a requirement that the restore point only be used once the initial pump clearing has been completed (e.g., based on the current time compared to a schedule for when this task to be completed).

If the therapy setting change does not concern a one-time event according to check 350, then the method 300 can determine whether a therapy medium is being changed in check 355. Various embodiments can, upon determining that a therapy medium is being changed, delete or otherwise invalidate previously stored restore points that are associated with the therapy medium being changed or are not associated with the new therapy medium.

A therapy medium can refer to various things depending on the type of therapy. For example, in the case of drug delivery, a therapy medium can refer to the changing of a drug or the changing of a catheter used to deliver the drug. In the case of electrical stimulation, a therapy medium can concern the changing of which electrode combinations are being used for delivery or the changing of a lead used for delivery. In any case, check 355 can identify situations wherein older restore points should be deleted or otherwise invalidated so that they are not later enacted. In regards to drug delivery, it may be unsafe to deliver a new and different drug using the delivery parameters that were developed for and used with the delivery of a previous drug, which could risk underdosing or overdosing the patient. Likewise, some lead changes can cause electrodes to be placed in different arrangements and previous delivery settings of a previous electrode configuration may be inappropriate for the new electrode configuration. In these and some other cases, it may be safer to invalidate 365 previous restore points so that they are not restored in an operational phase during therapy delivery if the therapy medium is being changed. In this way, not only may an external programmer automatically add restore points, but also manage restore points already saved on an implantable medical device by deleting them when their use could potentially be harmful to the patient. Furthermore, according to the particular flowchart of FIG. 3, the method 300 does not create 360 a new restore point if a therapy medium is being changed according to check 355 because the therapy settings being replaced would likely be inappropriate if the implantable medical device reverted to using them in a roll back in view of the therapy medium being changed. However, it is noted that not all envisioned embodiments are limited in these ways.

A change in therapy medium can be detected in various ways. The techniques for detecting the change may depend on the type of medium. If the change relates to a change in electrode combinations being used for therapy delivery, the electrodes slated for pulse delivery according to the therapy program instructions can be referenced to detect an electrode change. If a drug is being changed, then a log saved in the memory of the implantable medical device tracking drug fills of the reservoir can be referenced. In some embodiments, drug refill and drug depletion (e.g., by delivery or withdrawal) activities can be tracked by a sensor onboard the implantable medical device to keep an accurate assessment of fluid refills and quantity in the reservoir, which can be referenced by an external programmer for drug type and quantity assessment if needed. Such a log can be referenced to determine when a medium is being changed. Likewise, the swapping of a catheter or lead or other components can be noted in a log, where the clinician provides a notation of the change into the implantable medical device which can later be referenced by a programmer. The component being replaced can also be noted in the log as no longer being available (e.g., such that restore points and program versions specifically directed to these components could be invalidated and/or not relied upon to form a restore point or revert to a restore point). In some embodiments, a programmer may ask the clinician about components currently installed and note the information in the log. In some embodiments, a query can appear on a programmer asking the clinician whether a medium is being changed or is planned to be changed to perform check 355. It is noted that the options discussed herein as a therapy medium change may not be used in all cases, and something that qualifies as the therapy medium change in one embodiments (e.g., change in electrode combination used for stimulation) might not qualify as a therapy medium change in a different embodiment.

It is noted that the check 355 can be part of determining whether the implantable medical device will be able to operate using the program version being replaced to deliver therapy according to that program version if the implantable medical device was to revert back to using the program version being replaced, since the check 355 of a change in the therapy medium could identify a change that would not allow therapy to be delivered according to the therapy medium being replaced. In such a case, a restore point is not created based on the change of the therapy setting of the program version.

If the check 355 determines that the therapy medium is not being changed during the telemetry session, then a therapy setting restore point can be created 360 and saved on the implantable medical device based on the current (but being changed) therapy settings. Creating 360 and saving the therapy setting restore point can be done in any manner, including in any manner for creating 315 and storing a logical restore point (e.g., compress the program instructions needed to implement the therapy settings of the current program version as a restore point and save the restore point in a partitioned area of memory on the implantable medical device). As discussed herein, if the created 360 restore point were to be enacted based on a serious problem with the reprogrammed 345 new therapy settings, then the implantable medical device can deliver therapy using the same settings that were previously used and which are likely to be somewhat beneficial.

It is noted that the method 300 separates a program version into operational logic of firmware and therapy settings, each of which can independently be saved as a restore point and later used as needed without restoring of the other. Having restore points that restore just the operational logic or the therapy settings can be advantageous for several reasons. For example, in case the implantable medical device has a programming error hindering therapy delivery, but where the underlying therapy settings would be efficacious if only they could be delivered, then it may be preferable to restore only the operating logic of the implantable medical device (e.g., firmware controlling basic operations of the implantable medical device outside of therapy settings) while maintaining the therapy settings, as long as the current therapy settings are compatible with the operating instructions of the restore point. Also, in cases where the firmware of the implantable medical device is functioning properly, but the patient and/or clinician is not satisfied with a therapy change or current therapy parameters, then the patient and/or clinician can restore previous therapy settings without replacing the firmware of the implantable medical device. In some cases, it is preferable to only replace malfunctioning therapy parameter because of the central role that firmware plays in allowing an implantable medical device to function, and as such various embodiments herein can roll back therapy settings to a therapy settings restore point without changing the firmware, or with only changing the firmware as minimally as necessary to restore previous therapy settings, of the implantable medical device.

Each of the steps of the flowchart of FIG. 3, as well as the other features discussed in association with FIG. 3, can be performed automatically by control circuitry of an implantable medical device and/or an external programmer.

Therefore, as shown in FIG. 3, control circuitry can recognize and categorize different changes being made to the programming of an implantable medical device and can selectively save different types of restore points based on what is being changed in the implantable medical device. In view of these and other options, it will be understood that FIG. 3 illustrates one embodiment and that modifications of the method 300 are within the scope of this disclosure, including adding and/or omitting one or more steps of the illustrated embodiment.

In some cases, a previous program version will concern a complex schedule for therapy delivery, such as different parameters for a one-time event. In the creation of a restore point based on a program version, some embodiments will leave out the parameter changes for just the one-time event so that the other parameters of the program version can be packaged into a restore point. As such, if the restore point is loaded, the one-time event will not be recognized and enacted.

Although FIG. 3 demonstrates triggering the initiation of the creation of a restore point based on the detection of the program version being changed in a telemetry session, other embodiments may initiate the creation of a restore point based on other conditions. A restore point can be created for a current program version based on a particular input being received. A patient or clinician can provide an input to a programmer indicating satisfaction with a current program version, which might be based on the efficacy of the therapy parameters or the observed constancy and stability of the operation of the implantable medical device. A restore point can then be created and saved based on the current program version. In various embodiments, subsequent changes in a program version may or may not initiate the creation of a restore point, depending on the embodiment. In some cases, an input may initiate the evaluation of whether a restore point should be created, and the evaluation can follow any of the same steps of FIG. 3, including determining whether an essentially identical restore point already exists as in check 340.

Figure 4:
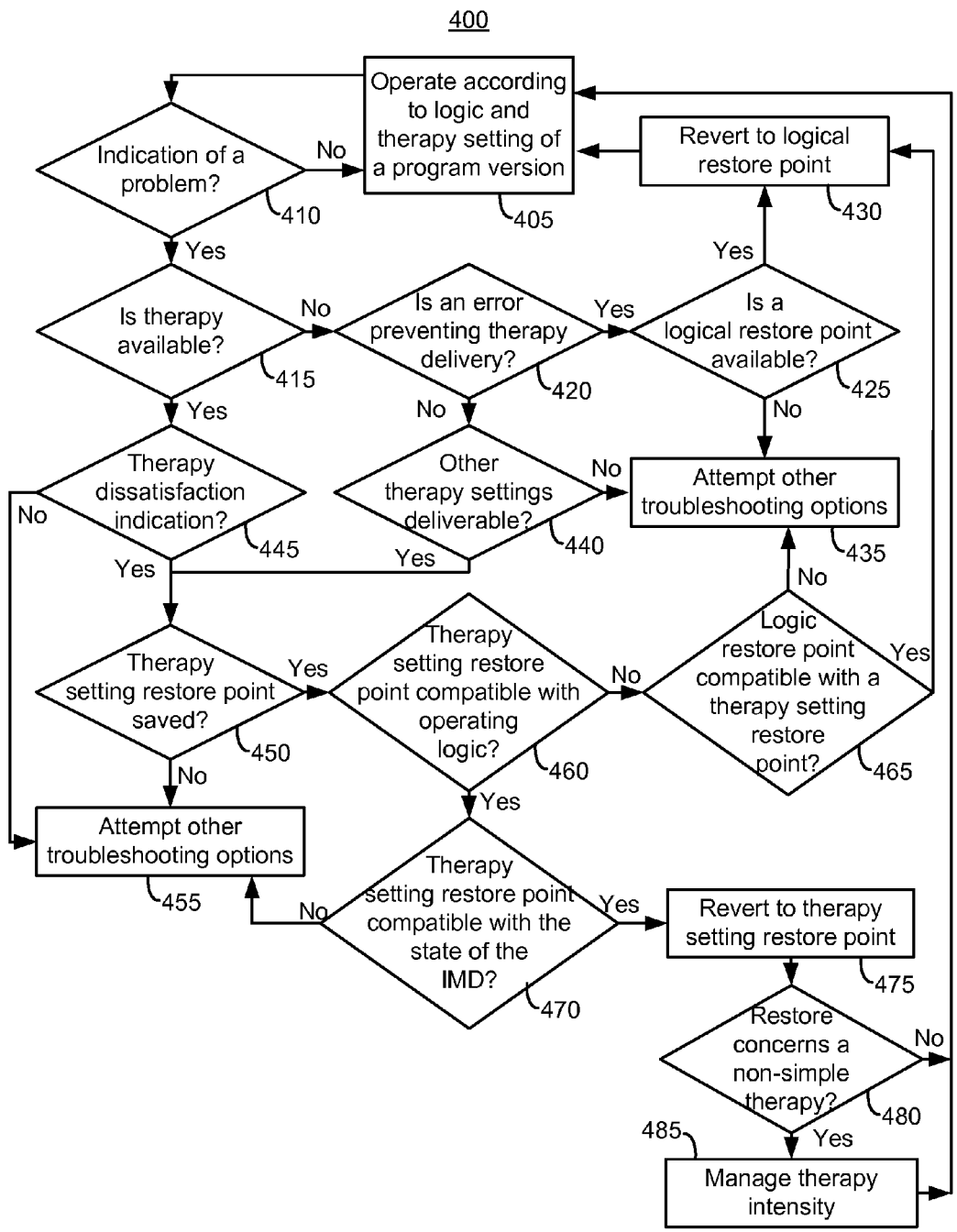
FIG. 4 is a flowchart of a method according to various embodiments for reverting programming of a medical device to a restore point.

FIG. 4 shows a flowchart of a method 400 for reverting operation of an implantable medical device to a restore point based on a previous program version. As will be shown, the method 400 can discriminate between conditions necessitating restoration of operational logic (e.g., basic firmware outside of therapy settings) and conditions necessitating restoration of therapy settings. As will be shown, FIG. 4 provides for restoring either or both of a logical restore point and a therapy setting restore point, which in various embodiments can be logical and therapy setting restore points created in a process identical or similar to the method 300 of FIG. 3. Independent restoration of operational logic or therapy settings of a program version can allow an implantable medical device to change only what needs to be changed to address a problematic condition.

The steps of the method 400 and other features discussed herein may be entirely performed automatically by control circuitry of an implantable medical device in an attempt to resolve one or more issues. However, in various other embodiments, some or all of the steps of the method 400 may be performed by control circuitry of an external programmer (e.g., patient or clinician programmer) which can use its often greater processing power to troubleshoot the implantable medical device via telemetry. In some cases, control circuitry distributed between the implantable medical device and the external programmer (e.g., each having respective processors and memory configured to work in coordination) may perform these or other method steps of this disclosure. In any case, the method 400 begins with the implantable medical device operating 405 according to the operational logic and therapy settings of a program version, the operating logic referring to the firmware controlling the basic functions of the implantable medical device and the therapy settings controlling the manner of delivery of a therapy by the implantable medical device. Periodically the implantable medical device can check 410 whether there is an indication of a problem. Check 410 can be performed by diagnostic circuitry, reception of error messages, from a patient or clinician indicating a problem (e.g., via an external programmer, a magnet, or other way of signaling the implantable medical device), time outs, race conditions, and/or any other way of identifying the presence of a problematic condition in the operation of an implantable medical device. As long as check 410 does not recognize an indication of a problem, operation 405 of the implantable medical device continues without loading a restore point. Error detection and detection of a problematic condition can be performed in the manner described in connection with FIG. 2, for example.

If the check 410 detects an indication of a problematic condition, then the method 400 determines whether therapy is available (e.g., presently being delivered or at least capable of being delivered as needed) at check 415. Check 415 can include internal diagnostics determining whether a pump is delivering fluid appropriately in the case of a drug pump or whether a neurostimulator is providing appropriate stimulation therapy. An implantable medical device may deliver a small sample of therapy to test whether the implantable medical device is capable of delivering the therapy. In any case, if the check 415 determines that therapy is not available, then this can be an indication that a fundamental issue with the implantable medical device may be occurring. In this case, the firmware may be malfunctioning or therapy hardware may be malfunctioning. To this end, the method 400 checks 420 whether an error is preventing therapy. An error preventing therapy delivery may be detected by the presence of logical alerts and errors, time outs, resets, intermittent failures, and/or data corruption, among other things.

Returning to check 415, if check 415 did determine that therapy is available, which can rule out many firmware issues, then the method 400 continues to check 445 to determine if an indication of therapy dissatisfaction has been received from a patient or clinician. The dissatisfaction indication may be the same indication of check 410. The dissatisfaction indication may be an input from an external programmer after a patient or clinician determines that a therapy change, such as a restoration of previous therapy parameters, would be preferable compared to the current therapy parameters. The current program version could be part of an experiment and the patient may wish to return to the previous therapy settings, and indicate this via a patient programmer. If no indication of therapy dissatisfaction has been received, then control circuitry of the implantable medical device and/or external programmer can attempt 455 other troubleshooting options which may be outside of the scope of this disclosure. Other troubleshooting options can include sending a message to an external programmer indicating that program version restoration was unable to resolve the problem indication.

If check 420 determines that a logical error may be preventing therapy delivery, such as by identifying a timeout or other processing error, then the method 400 advances to check 425 to determine whether a logical restore point is available. If, however, check 420 determines that a logical error is not preventing therapy delivery, a restoration of firmware is likely unneeded and the method 400 then checks 440 whether other therapy settings are deliverable. The current therapy settings may be unavailable because of a hardware problem (e.g., malfunction of some of the stimulation components, a break in a conductor of a lead, or decreased pump performance) that inhibits delivery of the current therapy settings but the problem may not be so severe that other therapy delivery settings (e.g., at a lesser amplitude, using different electrodes, or using a lower flow rate) cannot be used. As such, an analysis can determine whether the implantable medical device can still deliver some aspect or level of therapy (e.g., by testing to see whether different therapy functions can be performed), and if it can, then the method 400 can advance to check 450, which determines whether any therapy setting restore points are saved. If other therapy settings are not deliverable according to check 440, then the method 400 can attempt 435 other troubleshooting options, which as mentioned previously may be outside of the scope of this disclosure, but might include generating an alert message indicating that program version restoration was unable to resolve the problem indication.

Returning to check 425, the check 425 determines whether a logical restore point is available. This check 425 can include determining whether any logical restore points are saved in memory. In various embodiments, check 425 includes determining whether any saved logical restore points are compatible with a current configuration of the implantable medical device. For example, some firmware may only be appropriate for certain leads or while a particular drug is within the implantable medical device. If the implantable medical device is not properly configured to function in a manner consistent with any of the saved logical restore points, then check 425 may be failed (if such a check is performed) and the method 400 can attempt 435 other troubleshooting options. If, however, a logical restore point is available, and if check 425 determines that the logical restore point is compatible with the current configuration of the implantable medical device, then control circuitry can revert 430 firmware or other basic logical operation of the implantable medical device from a current program version (e.g., that being run in the operating 405 step) to the logical restore point that passed check 425. If multiple logical restore points passed check 425, then the most recently saved, oldest, or longest used logical restore point can be restored in reversion 430. The implantable medical device can then operate 405 according to the restored logic. The steps of the method 400 can be repeated down the same or different branches if the same or different problem is indicated again in check 410.

Returning to check 450, check 450 determines whether a therapy setting restoration point is saved on the implantable medical device. This can include determining whether any restoration points are saved in memory that restore therapy settings that are different from the therapy settings currently being used. If no therapy setting restore points are present on the implantable medical device, then the method 400 can attempt 455 other troubleshooting options.

If one or more therapy setting restore points are saved on the implantable medical device according to check 450, then the saved one or more restore points and the state of the implantable medical device can be evaluated and the restore points filtered in a number of checks. Check 460 can determine whether any of the therapy setting restore points is compatible with the current operating logic of the implantable medical device. Some firmware might not be compatible with all therapy settings. For example, some therapy settings may require more stimulation power than the firmware is programmed to allow the stimulation circuitry to draw from the battery. Some therapy settings may require a mechanical pump onboard to the implantable medical device to operate at a higher capacity than the firmware is programmed to allow.

If none of the therapy setting restore points are compatible with the current operating logic, then check 465 can consider whether any of the logical restore points are compatible with any therapy setting restore points. If there are no matches of logical restore points and therapy setting restore points stored on the implantable medical device, then the method 400 can attempt 435 other troubleshooting options. If a logic restore point is compatible with a therapy setting restore point according to check 465, then the implantable medical device can revert 430 to the compatible logic restore point and the method 400 can proceed according to a flow that progresses to reversion 475 of the compatible therapy setting restore point (or the reversion to the compatible therapy setting restore point can be performed at the same time as, or immediately after, the reversion 430 to the compatible logic restore point).

Returning to check 460, if check 460 determines that one of the therapy setting restore points is compatible with the current operating logic, then the method 400 can check 470 whether the therapy setting restore point is compatible with the current implantable medical device configuration. Determining compatibility between the therapy setting restore point and the current implantable medical device state can include determining whether the current configuration of the implantable medical device is capable of delivering therapy consistent with the therapy setting restore point. For example, such an evaluation could determine whether the implantable medical device has enough power remaining, has enough drug of the proper type to deliver, has the correct electrodes enabled, and/or has the appropriate delivery attachment (e.g., lead or catheter) to implement the delivery parameters of the therapy setting restore point. In some embodiments, a lookup table can be saved on the implantable medical device listing configuration requirements for particular therapy settings. The lookup table can be used to determine whether therapy settings, such as those of a restore point, can be output by different implantable medical device configurations. Check 470 may be performed by comparing the current configuration of the implantable medical device to an index of information that is part of the restore point, the index detailing the configuration of the implantable medical device at the time the therapy settings of the therapy setting restore point were used. If the configurations are the same, or at least similar enough for matters that concern delivery of the therapy settings of the restore point sufficient to deliver the therapy, then check 470 can be passed. If the check 470 determines that the current state of the implantable medical device is not compatible with any therapy setting restore points (or any therapy setting restore point that has passed checks 460), then other troubleshooting options can be attempted 455.

If a therapy setting restore point is compatible with the current operating logic and the current state of the implantable medical device, thereby passing checks 460 and 470, then the implantable medical device can revert 475 to using the therapy setting restore point to control therapy delivery. For example, the therapy settings of the therapy setting restore point may require a more intense therapy (e.g., high rate of drug delivery or higher stimulation amplitude) relative to the therapy settings being used when the indication of the problem was received. The change in the therapy settings may be able to resolve several problems, such as patient dissatisfaction with the therapy or an implantable medical device having difficulty maintaining the current delivery settings (e.g., too low or high of a drug volume for a pump to consistently deliver) where the implantable medical device may be more effective at using previous parameter settings of a therapy setting restore point.

In some embodiments, reversion 475 to a therapy setting restore point can change a closed loop setting of therapy delivery. For example, if a therapy output is based on a sensor input (e.g., brain state as determined by sensed brain signal) according to a relationship (e.g., a particular linear relationship between the intensity of sensed epileptic activity in the brain and the intensity of an anti-seizure stimulation output in response thereto), then the therapy settings of a restore point can change the particular relationship between the input and output. If the therapy concerns spinal cord stimulation based on the posture of the patient, then loading a different therapy settings from a restore point can cause an implantable medical device to output different stimulation levels in response to various postures as compared to the stimulation levels used before loading the restore point.

In some embodiments, a check 480 is performed to determine whether the therapy setting restore point restores from a non-simple therapy and/or restore to a non-simple therapy. A non-simple therapy is a therapy whereby the intensity of the therapy changes over time. The therapy may change according to a schedule (e.g., more intense during daytime hours and less intense during nighttime hours), according to a detected condition (e.g., closed loop titration according to a detected event), according to patient indications (e.g., patient controlled dosage via patient programmer), or other technique for changing therapy parameters. If the restore point reverts 475 operation of the implantable medical device to a non-simple therapy, then the patient could potentially receive an unexpectedly large amount of therapy immediately following the reversion, which might be a particular problem if the patient already was receiving higher levels of therapy before the reversion. Protections might be in place for a single therapy setting that prevents too much or too little therapy to be delivered within a window of time (e.g., a limit on the amount of drug that can be delivered within a window of time), but such protections might be circumvented if the therapy settings change as part of the reversion 475. In such a case, managing 485 therapy intensity can protect against overdosing or underdosing the patient by two periods of relatively high intensity from being consecutively delivered or from two periods of relatively low intensity from being consecutively delivered just before and after reversion 475. Managing 485 therapy intensity can include temporarily lowering relatively high therapy intensity settings (e.g., amplitude, current, dosage, flow rate) or raising relatively low therapy intensity settings. The raising or lowering amounts can be 25% or 50% of the therapy settings of the restore point, for example. The therapy intensity can then be gradually changed to align with the therapy settings of the restore point.

In some cases, a non-simple therapy will allow a patient to control the intensity of the therapy via a patient programmer but control circuitry will not let the total amount of therapy delivered exceed a predetermined amount over a period of time. For example, a non-simple drug therapy to manage pain can allow the patient to control the amount of drug delivered but control circuitry will lock-out the patient's control and automatically determine appropriate rates of drug delivery if a predetermined amount of the drug has been delivered within a limited amount of time (e.g., 20 microliters within an hour). If a reversion 475 implements a non-simple therapy with a patient control and lock-out threshold, then the control circuitry may continue to keep track of how much drug has been delivered, before and after the reversion 475, so that a patient cannot exceed the lock-out threshold due to the reversion 475. If the different therapy settings used before and after the reversion 475 had different limits on how much drug or other therapy could be delivered, then the different limit amounts might be averaged for a period of time following reversion 475 as part of managing 485 therapy intensity. In this way, information regarding how much therapy has been recently delivered may not be replaced in a reversion 475, according to some embodiments. If this information is necessarily lost by a logical or therapy setting reversion, then the management 485 step can control the intensity of delivery at a low, moderate, or averaged level for a predetermined amount of time (e.g., until a lock-out period, started at the time of reversion 475, would have expired).

In some cases, the therapy settings can be averaged between the therapy settings used prior to reversion 475 and the therapy settings of the restore point to which the implantable medical device reverted 475. Such averaging or other form of smoothing can be performed between two disparate therapy settings to prevent a sharp change in therapy intensity, which might be uncomfortable to the patient.

If the check 480 determines that the therapy setting restore point of the reversion 475 concerns a simple therapy, then it is assumed that the intensity has already been cleared for sustained delivery to the patient and intensity mitigation 485 is not needed. In this case, the method 400 loops back to operating 405 according to the current therapy settings of the therapy setting restore point of the reversion 475. In view of these and other options, it will be understood that FIG. 4 illustrates one embodiment and that modifications of the method 400 are within the scope of this disclosure, including adding and/or omitting one or more steps of the illustrated embodiment.

It is noted that in some embodiments, some information concerning therapy delivery will be maintained despite a reversion to a restore point. Such information may concern the amount of therapy already delivered (e.g., the amount of drug taken from a reservoir or the amount of stimulation delivered) or the amount of medium remaining (e.g., the amount of energy remaining in a battery or the amount of fluid in a reservoir). Preserved information may include sensed data, device lifecycle information (e.g., concerning service life), limits on how much therapy can be delivered within a time frame (e.g., prescribed drug quantity limits), device life cycle information, alarm information, and/or information concerning what type of drug is within the implantable medical device. Keeping this information can avoid situations where an implantable medical device would otherwise restore a previously used program version that, at the time the restore point was created, a certain amount of medium was believed to remain in the device. However, since the amount of medium is likely to have changed via therapy delivery, maintaining such information despite a reversion can avoid a situation where the implantable medical device indicates or relies on an inaccurate assessment of the amount of medium remaining. In some cases, information that may be retained despite a reversion include, but is not limited to, battery information (e.g., usage and/or recharge logs, voltage measurements), alarm settings and conditions, information about the patient and other topics, and/or self-diagnostic information about the implantable medical device.

It is noted that not all embodiments will perform each of the steps of the methods presented herein, and modifications to the methods are contemplated, whether by omitting and/or adding steps. Each of the methods discussed herein can concern the same embodiments, with the different flowcharts highlighting different aspects reprogramming an implantable medical device. Each of the methods discussed herein can be fully or partially implemented in control circuitry of an implantable medical device (e.g., a neurostimulator configured for DBS) and/or an external device.

A variety of medical devices are used for chronic delivery of therapy (e.g., fluid or stimulation) to patients suffering from a variety of conditions, such as chronic pain, tremor, Parkinson's disease, epilepsy, urinary or fecal incontinence, sexual dysfunction, obesity, spasticity, or gastroparesis. For example, pumps or other fluid delivery devices can be used for chronic delivery of therapeutic fluids, such as drugs to patients. These devices are intended to provide a patient with a therapeutic output to alleviate or assist with a variety of conditions. Typically, such devices are implanted in a patient and provide a therapeutic output under specified conditions on a recurring basis. A drug infusion device or a stimulation device, as an implantable medical device, may be partially or completely implanted at a location in the body of a patient and deliver a fluid medication through a catheter or stimulation through a lead to a selected delivery site in the body.

In various embodiments, an implantable medical device may be used to deliver stimulation or therapeutic substances to the spinal cord, cranial nerve, the brain, vasculature, peripheral nerve, or other areas of the body. As further examples, a catheter or lead may be positioned for temporary or chronic spinal cord therapy for the treatment of pain, for peripheral neuropathy or post-operative pain mitigation, ilioinguinal nerve stimulation, intercostal nerve stimulation, gastric stimulation for the treatment of gastric mobility disorders and obesity, muscle stimulation (e.g., functional electrical stimulation (FES) of muscles), for mitigation of other peripheral and localized pain (e.g., leg pain or back pain), or for deep brain stimulation to treat movement disorders and other neurological disorders. In various embodiments, an implantable medical device having programming restoration capabilities as discussed herein does not need to deliver a therapy, or deliver any of the particular therapies referenced herein. For example, an implantable medical device can sense a physiological signal and transfer sensed or derivative information to an external device or retain recorded information proximal to the detection of events for subsequent access. The programming of the implantable medical device, including sensing, data collection, and data processing programming, can be restored as discussed herein. All such applications listed above or otherwise referenced herein, as well as others that will occur to one having ordinary skill in the art, are envisioned as within the scope of the programming reversion teachings of this disclosure.

An implantable medical device may be implanted in the body of a patient to deliver a fluid, such as a drug or other therapeutic agent, through a catheter to one or more selected delivery sites within the body of the patient. The implantable medical device may include a reservoir for storing the therapeutic agent prior to delivery to the patient. The implantable medical device may also include a refill port to facilitate in-service refilling of the fluid reservoir over the service life of the implantable medical device. The port may be connected to the reservoir by a fluid pathway. A needle or syringe may be percutaneously inserted into the port to add therapeutic agent to the fluid reservoir through the fluid pathway. Alternatively, the port can be used to remove therapeutic agent from fluid reservoir. For example, a therapeutic agent may be removed from the fluid reservoir prior to refilling the fluid reservoir with a different type of therapeutic agent. In some cases, multiple fluid reservoirs containing identical or different therapeutic agents may be used.

Figure 5:
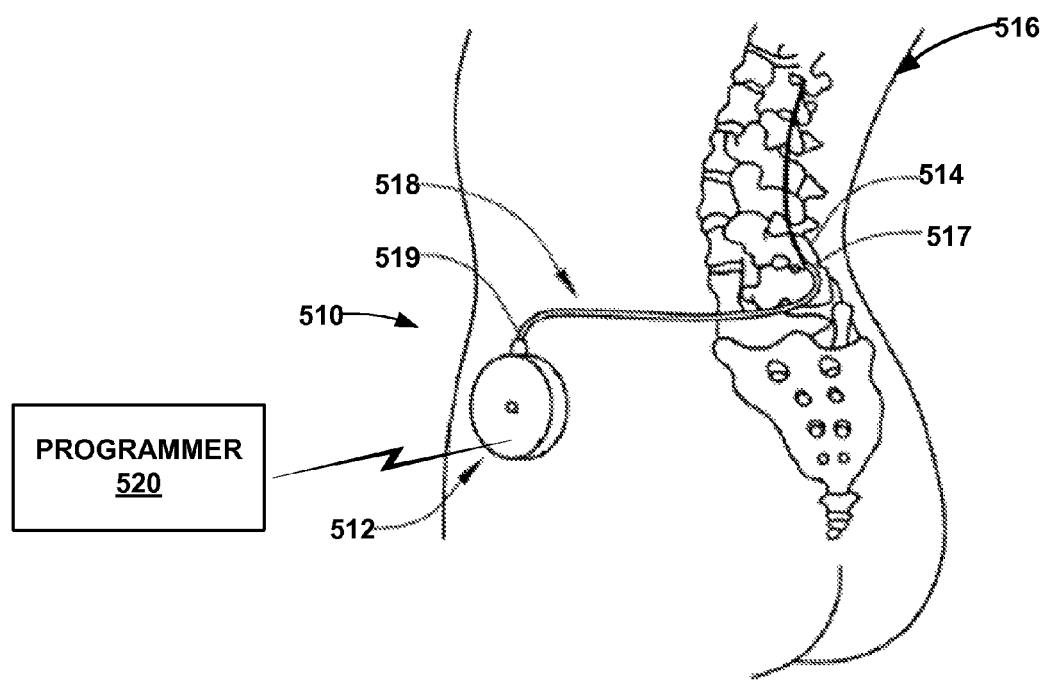
FIG. 5 is a conceptual diagram illustrating an example of a fluid delivery system including an implantable medical device configured to deliver a therapeutic fluid to a patient via a catheter.

FIG. 5 illustrates a conceptual diagram of a therapy system 510, which includes external programmer 520 and implantable medical device 512 implanted in a patient 516 and positioned to deliver a therapy to the patient 16. Although the implantable medical device 512 will be discussed herein as a drug infusion pump, it is understood that the implantable medical device 512 could be any other type of medical device, such as an electrical stimulator. U.S. Pat. No. 8,000,788 to Giftakis, et al, which is herein incorporated by reference in its entirety, presents multiple different stimulation applications, variations of which programming reversion could be applied. The techniques and circuitry disclosed herein for programming restoration are applicable to essentially all medical devices having programming, and all such medical devices may be within the scope of this disclosure. The implantable medical device 512 is principally presented herein as an infusion pump for the sake of providing an example system to demonstrate various aspects of the present disclosure.

Implantable medical device 512 is connected to at least one catheter 518 to deliver at least one therapeutic fluid, e.g. a pharmaceutical agent, pain relieving agent, anti-inflammatory agent, gene therapy agent, or the like, to a target site within patient 516. Implantable medical device 512 includes an outer housing that, in some examples, is constructed of a biocompatible material that resists corrosion and degradation from bodily fluids including, e.g., titanium or biologically inert polymers. Implantable medical device 512 may be implanted within a subcutaneous pocket relatively close to the therapy delivery site. For example, as shown in FIG. 5, implantable medical device 512 may be implanted within an abdomen of patient 516. In other examples, implantable medical device 512 may be implanted within other suitable sites within patient 516, which may depend, for example, on the target site within patient 516. In still other examples, implantable medical device 512 may be external to patient 516 with a percutaneous delivery element (e.g., catheter or lead) connected between device 512 and the target delivery site within patient 516.

Implantable medical device 512 delivers a therapeutic fluid from a reservoir to patient 516 through catheter 518 from proximal end 519 coupled to implantable medical device 512 to distal end 517 located proximate to the target site. Example therapeutic fluids that may be delivered by implantable medical device 512 include, e.g., insulin, morphine, hydromorphone, bupivacaine, clonidine, other analgesics, baclofen and other muscle relaxers and antispastic agents, genetic agents, antibiotics, nutritional fluids, hormones or hormonal drugs, gene therapy drugs or agents, anticoagulants, cardiovascular medications or chemotherapeutics.

Catheter 518 can comprise a unitary catheter or a plurality of catheter segments connected together to form an overall catheter length. Catheter 518 may be coupled to implantable medical device 12 either directly or with the aid of a catheter extension (not shown in FIG. 5).

Programmer 520 is an external computing device that is configured to communicate with implantable medical device 512 by wireless telemetry as needed, such as to reprogram the implantable medical device 512, program the implantable medical device 512 with one or more restore points, adjust therapy parameters, retrieve therapy information from the implantable medical device 512, and/or control any other aspects of the implantable medical device (e.g., turn implantable medical device 512 on or off, and so forth) from implantable medical device 512 to patient 516. In some examples, programmer 520 may be a clinician programmer that the clinician uses to communicate with implantable medical device 512, reprogram the implantable medical device 512, communicate an indication of a problematic condition (e.g., an error, lack of therapy delivery, or otherwise indicate a desire to roll back to a restore points), and set restore points. Alternatively, programmer 520 may be a patient programmer that allows patient 516 to perform some of the functions of a clinician programmer (e.g., adjust therapy). The clinician programmer may include additional or alternative programming features than the patient programmer. For example, more complex or sensitive tasks may only be allowed by the clinician programmer to prevent patient 516 from making undesired or unsafe changes to the operation of the implantable medical device 512. For example, in some embodiments a clinician programmer may be able to set restore points and initiate a reversion to a restore point while a patient programmer may not perform either of these functions (e.g., only allowing therapy adjustment). Programmer 520 may be a handheld or other dedicated computing device, or a larger workstation or a separate application within another multi-function device.

Figure 6:
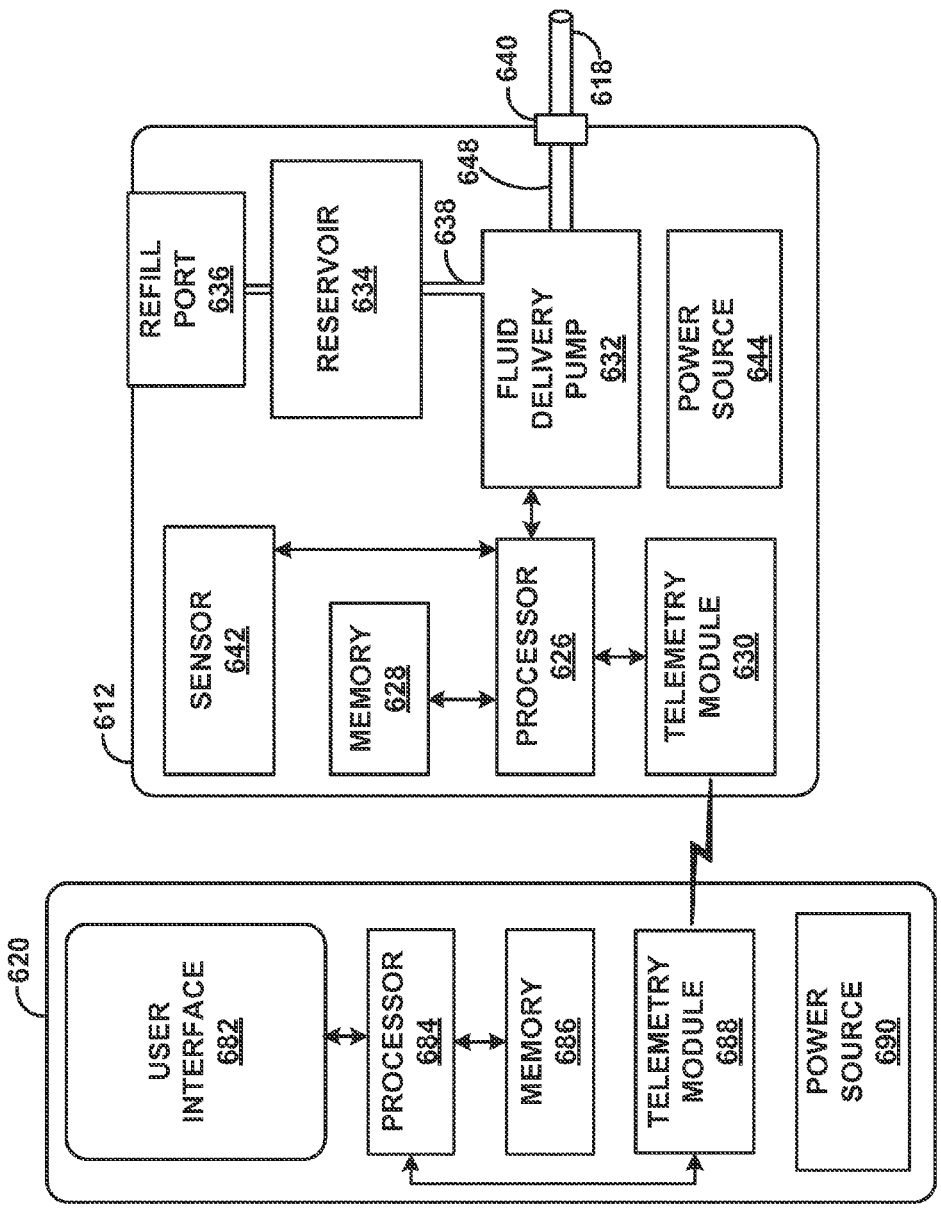
FIG. 6 is a functional block diagram illustrating an example of an implantable medical device and external programmer.

FIG. 6 is a functional block diagram illustrating components of an example of implantable medical device 612, which can be the same implantable medical device 512 of FIG. 5, which may perform the operations discussed herein. The implantable medical device 612 includes processor 626, memory 628, telemetry module 630, fluid delivery pump 632, reservoir 634, reservoir fluid pathway 638, catheter connection 640, catheter 618, sensor 642, and power source 644. Processor 626 is communicatively connected to memory 628, telemetry module 630, fluid delivery pump 632, and sensor 642. Fluid delivery pump 632 is connected to reservoir 634 and internal fluid pathways 648. Implantable medical device 612 also includes power source 644, which is configured to deliver operating power to various components of the implantable medical device. Upon instruction from processor 626, fluid delivery pump 632 draws fluid from reservoir 634 and pumps the fluid through internal fluid pathways 648 to catheter 618 through which the fluid is delivered to patient 516 to effect one or more of the treatments described above in accordance with a program version stored on memory 628.

In various embodiments, fluid delivery pump 632 may be an axial pump, a centrifugal pump, a pusher plate pump, a piston-driven pump, or other means for moving fluid through internal fluid pathways 648 and catheter 618. In one example, fluid delivery pump 632 is an electromechanical pump that delivers fluid by the application of pressure generated by a piston that moves in the presence of a varying magnetic field and that is configured to draw fluid from reservoir 634 and pump the fluid through internal fluid pathways 648 and catheter 618 to patient 516.

During operation of the implantable medical device 612, processor 626 controls fluid delivery pump 632 with the aid of program instructions of a program version that is stored in memory 628 to deliver a therapeutic fluid to patient 616 via catheter 618 according to therapy settings of the program version. Instructions executed by processor 626 may, for example, define the therapy settings that specify the dose of therapeutic fluid that is delivered to a target tissue site within patient 516 from reservoir 634 via catheter 618. The therapy settings may further specify a schedule of different therapeutic fluid rates and/or other parameters by which implantable medical device 612 delivers therapy to patient 516.

In general, a program version stored on memory 628 and executed by processor 626 defines one or more therapeutic fluid doses to be delivered from reservoir 634 to patient 516 through catheter 618 by implantable medical device 612 for infusion embodiments. However, other embodiments within the scope of this disclosure may concern a program version stored on memory 628 and executed by processor 626 that defines one or more stimulation parameter settings for controlling an output of a pulse generator of an implantable medical device 612 in an electrical stimulation embodiment. Memory 628 and processor 626 and may contain and execute instructions of a program version, with the capability of reversion to a restore point as discussed herein, in connection with various therapy systems, including but not limited to drug delivery and stimulation delivery. In this way, processor 626 and memory 628 can be control circuitry that controls the functions of the implantable medical device 612.

In the embodiment of FIG. 6, implantable medical device 612 includes sensor 642 communicatively coupled to processor 626. Sensor 642 may be arranged in a number of locations within implantable medical device 612, including, e.g., in reservoir 634, reservoir fluid pathway 638, catheter connection 640, or internal fluid pathways 648. In some embodiments, implantable medical device 612 may include multiple sensors, e.g., to measure different fluid characteristics or to measure fluid characteristics in multiple locations. Regardless of where arranged, sensor 642 may be configured to measure at least one fluid characteristic in implantable medical device 612, which can be useful in troubleshooting and determining whether therapy is available and/or being delivered (e.g., as in check 415 of FIG. 4). In various examples, sensor 642 may be a pressure sensor, flow sensor, capacitive sensor, acoustic sensor, optical sensor, pH sensor, temperature sensor or the like. Sensor 642 generates a signal indicative of a fluid characteristic, and the signal is transmitted to processor 626, e.g., for analysis and storage on memory 628. In some embodiments, sensor 642 may be a physiologic sensor for sensing a physiologic parameter, such as heart rate, pressure, electrical activity (e.g., of the heart, brain, nerve, or other organ or tissue), chemical parameter (e.g., blood oxygen saturation), patient movement or activity, patient posture, and/or any other parameter.

Periodically, fluid may need to be percutaneously added or withdrawn from implantable medical device 612. Fluid may need to be withdrawn from reservoir 634 if a clinician wishes to replace an existing fluid with a different fluid or a similar fluid with different concentrations of therapeutic agents. Fluid may also need to be added to reservoir 634 if all therapeutic fluid has been or will be delivered to patient 616. Refill port 636 provides access for adding or withdrawing fluid from the reservoir 634. Processor 626, memory 628, and sensor 642 may be employed to determine when fluid is being added to the reservoir 634 via refill port 636 and/or removed from the reservoir 634 by fluid deliver pump 632 during the course of therapy delivery and/or from the reservoir 634 via refill port 636 during a switching of fluid. This information may be stored in memory 628 and used to determine the state of the implantable medical device 612 (e.g., which drug, and how much, is present in the reservoir 634) and further to determine whether a program version, or a particular therapy setting of a program version, is compatible with a current state of the implantable medical device 612.

In general, memory 628 stores program instructions and related data that, when executed by processor 626, cause implantable medical device 612 to perform the functions in this disclosure as control circuitry. For example, memory 628 of implantable medical device 612 may store instructions for execution by processor 626 including, e.g., a program version, one or more restore points, and any other information regarding therapy delivered to patient 516 and/or the operation of implantable medical device 612. Memory 628 may include separate memories for storing instructions, patient information, program versions, information about the state of the device, therapy settings, restore points, and other categories of information such as any other data that may benefit from separate physical memory modules.

Processor 626 controls telemetry module 630 to wirelessly communicate between implantable medical device 612 and other devices, such as programmer 620. Telemetry module 630 in implantable medical device 612, as well as telemetry circuitry in other devices, such as programmer 620, can be configured to use, e.g., RF communication techniques and/or near field communication techniques to wirelessly send and receive information to and from other devices respectively according to standard or proprietary telemetry protocols. In addition, telemetry module 630 may communicate with programmer 620 via proximal inductive interaction between implantable medical device 612 and the external programmer. Telemetry module 630 may send information to external programmer 620 on a continuous basis, at periodic intervals, or upon request from the programmer. Telemetry module 630 may include appropriate electronic components to support wireless communication, such as amplifies, filters, mixers, encoders, decoders, modulators, demodulators and the like.

Memory 628 of implantable medical device 612 and/or memory 686 of programmer 620 may include any volatile or non-volatile media, such as a random access memory (RAM), read only memory (ROM), non-volatile random access memory (NVRAM), electrically erasable programmable read only memory (EEPROM), flash memory, and the like. Memory 628 may be used to store one or more restore points. Memory 628 of implantable medical device 612 may include multiple memory structures, such as a first memory structure comprising RAM onto which a current program version is loaded and program instructions of the current program version are actively executed by the processor 626 to control operation of the implantable medical device 612. Memory 628 may include a second memory structure upon which is stored one or more restore points that are not loaded onto the first memory structure to control the implantable medical device 612 unless a reversion is performed as discussed herein. In some embodiments, the memory 628 is a single memory structure where the program instructions of a current program version being actively used by the processor 626 to control the operation of the implantable medical device are stored, the single memory structure also storing one or more restore points which are not actively used.

Power source 644 delivers operating power to various components of implantable medical device 612. Power source 644 may include a rechargeable battery or non-rechargeable battery and a power generation circuit to produce the operating power. In the case of a rechargeable battery, recharging may be accomplished through a variety of techniques including, e.g., proximal inductive interaction or kinetic energy-scavenging device. As another alternative, an external inductive power supply can transcutaneously power implantable medical device 612 as needed or desired.

As described herein, implantable medical device 612 may communicate with one or more external devices. FIG. 6 further illustrates a functional block diagram of an external programmer 620, which may be the programmer 520 of FIG. 5. As shown in FIG. 6, programmer 620 may include user interface 682, processor 684, memory 686, telemetry module 688, and power source 690. A clinician or patient interacts with user interface 682 (e.g., a touch screen to display information and to allow user input) to control the programmer 620 and well as interact with the implantable medical device 612 via respective telemetry modules 630 and 688. Such interactions can include changing the parameter settings of a program version, indicating satisfaction or dissatisfaction with a therapy setting or current or past operation of the implantable medical device 612, set restore points, reprogram logical program instructions (e.g., firmware) of the implantable medical device 612, retrieve information from the implantable medical device 612 (e.g., sensed data, identified errors, and/or information concerning the current configuration of the implantable medical device 612), and/or other functions. Processor 684 controls user interface 682, retrieves data from memory 686, and stores data within memory 686. Processor 684 also controls the transmission of data through telemetry module 688 to implantable medical device 612. The transmitted data may also include therapy program information specifying various therapeutic fluid delivery parameters. Memory 686 may store operational instructions for processor 684 and program instructions for reprogramming the implantable medical device 612. In general, memory 686 stores program instructions and related data that, when executed by processor 684, cause programmer 620 and possibly implantable medical device 612 to perform the functions of this disclosure as control circuitry. In some cases, the functions described herein can be carried about by processors 684 and memory 628 and 686 working in coordination as control circuitry distributed between the implantable medical device 612 and the programmer 620 (e.g., facilitated via telemetry modules 630 and 688).

When configured as a clinician programmer, programmer 620 may transmit an identification number, authorization code, or like identifying information via telemetry module 688 to implantable medical device 612 to authenticate that programmer 620 is a clinician programmer and thereby authorize reprogramming of the implantable medical device 612.

Telemetry module 688 allows the transfer of data to and from programmer 620 and implantable medical device 612, as well as other devices, e.g. according to the RF communication techniques. Power source 690 may be a non-rechargeable battery or a rechargeable battery. In some examples, programmer 20 may be configured to recharge implantable medical device 612 in addition to reprogramming implantable medical device 612. Telemetry module 688 may include appropriate electronic components to support wireless communication, such as amplifies, filters, mixers, encoders, decoders, modulators, demodulators and the like.

The techniques described in this disclosure, including the method steps of FIGS. 1-4 and those attributed to a programmer, an implantable medical device, processor, and/or control circuitry, or various constituent components, may be implemented wholly or at least in part, in hardware, software, firmware or any combination thereof, such as the modules of FIG. 6. A processor, as used herein, refers to any number and/or combination of a microprocessor, a digital signal processor (DSP), an application specific integrated circuit (ASIC), a field-programmable gate array (FPGA), microcontroller, discrete logic circuitry, processing chip, gate arrays, and/or any other equivalent integrated or discrete logic circuitry. "Control circuitry" as used herein refers to at least one of the foregoing logic circuitry as a processor, alone or in combination with other circuitry, such as memory or other physical medium for storing instructions, as needed to carry about specified functions (e.g., processor and memory having stored program instructions executable by the processor for creating a restore point based on a program version, determining whether an implantable medical device could deliver therapy according to a previous program version, and reverting operation of the implantable medical device to the previous program version as a restore point). The functions referenced herein and those functions of FIGS. 1-4, may be embodied as firmware, hardware, software or any combination thereof as part of control circuitry specifically configured (e.g., with programming) to carry out those functions, such as in means for performing the functions referenced herein. The steps described herein may be performed by a single processing component or multiple processing components, the latter of which may be distributed amongst different coordinating devices (e.g., an implantable medical device and an external programmer). In this way, control circuitry may be distributed between multiple devices, including an implantable medical device and an external medical device in various systems. In addition, any of the described units, modules, or components may be implemented together or separately as discrete but interoperable logic devices of control circuitry. Depiction of different features as modules or units is intended to highlight different functional aspects and does not necessarily imply that such modules or units must be realized by separate hardware or software components and/or by a single device. Rather, functionality associated with one or more module or units, as part of control circuitry, may be performed by separate hardware or software components, or integrated within common or separate hardware or software components of the control circuitry.

When implemented in software, the functionality ascribed to the systems, devices and control circuitry described in this disclosure may be embodied as instructions on a physically embodied (i.e., "non-transitory") computer-readable medium such as RAM, ROM, NVRAM, EEPROM, flash memory, magnetic data storage media, optical data storage media, or the like, the medium being physically embodied (i.e., "non-transitory") in that it is not a carrier wave, as part of control circuitry. Examples of computer-readable medium include, but are not limited to, memories 628 and 686 described herein. The instructions may be executed to support one or more aspects of the functionality described in this disclosure.

I claim:

1. A method comprising:
reprogramming an implantable medical device to operate using a second program version, the second program version replacing a first program version in controlling operation of the implantable medical device, the implantable medical device reprogrammed by an external programmer;
determining whether the implantable medical device will be able to operate using the first program version to deliver therapy according to the first program version if the implantable medical device was to revert back to using the first program version; and
reverting operational programming of the implantable medical device from the second program version to the first program version, the first program version saved in memory internal to the implantable medical device as a restore point while the implantable medical device operates according to the second program version between the reprogramming and reverting of the implantable medical device.

2. The method of claim 1, wherein:
the restore point is created during a telemetry session between the implantable medical device and the external programmer;
the determining step is performed during the telemetry session;
the reprogramming step is performed during the telemetry session; and
the restore point is only created if it is determined that the implantable medical device will be able to operate using the first program version to deliver therapy according to the first program version.

3. The method of claim 1, further comprising detecting a problematic condition, wherein the reverting step is performed based on the detection of the problematic condition.

4. The method of claim 3, wherein detecting the problematic condition comprises the implantable medical device detecting one or more errors preventing an intended operation of the implantable medical device.

5. The method of claim 3, wherein detecting the problematic condition comprises the implantable medical device receiving an external signal indicating dissatisfaction with operation of the implantable medical device.

6. The method of claim 3, wherein:
the determining step is performed based on the detection of the problematic condition; and
the reverting step is only performed if the determining step determines that the implantable medical device will be able to operate using the first program version to deliver therapy according to the first program version.

7. The method of claim 1, wherein the determining step further comprises:
determining which program versions of a plurality of program versions saved in memory of the implantable medical device as a plurality of restore points the implantable medical device will be able to use to deliver therapy according to each respective program version of the plurality of program versions; and
deleting or invalidating any of the plurality of restore points for which the determination step determines that the implantable medical device will not be able to use to deliver therapy according to the respective program version.

8. The method of claim 1, wherein the determining step comprises determining whether a therapy medium of the implantable medical device which the first program version would use has been changed.

9. The method of claim 1, wherein the determining step comprises determining whether a drug stored within the implantable medical device or an electrode configuration has been changed.

10. The method of claim 1, wherein the first program version includes firmware that controls basic functions of the implantable medical device.

11. The method of claim 1, wherein the first program version includes program instructions that control therapy settings for the implantable medical device.

12. The method of claim 1, wherein reverting operational programming of the implantable medical device from the second program version to the first program version only restores the therapy settings of the first program version and does not change operational logic that controls other functions of the implantable medical device.

13. The method of claim 1, further comprising programming the implantable medical device with the first program version, the first program version controlling operation of the implantable medical device until the reprogramming step.

14. A system comprising:
an implantable medical device configured to deliver therapy to a patient, the implantable medical device configured to operate according to a first program version loaded on the implantable medical device;
an external programmer, the external programmer configured to reprogram the implantable medical device via telemetry to operate according to a second program version that replaces the first program version in controlling operation of the implantable medical device; and
control circuitry located in either or both of the implantable medical device and the external programmer, the control circuitry configured to determine whether the implantable medical device will be able to operate using the first program version to deliver therapy according to the first program version if the implantable medical device was to revert back to using the first program version, wherein the implantable medical device is configured to revert from operating according to the second program version to operating according to the first program version, the first program version saved in memory internal to the implantable medical device as a restore point as the implantable medical device operates according to the second program version.

15. The system of claim 14, wherein
the control circuitry is configured to create the restore point during a telemetry session between the implantable medical device and the external programmer,
the external programmer is configured to reprogram the implantable medical device during the telemetry session, and
the control circuitry is configured to create the restore point only if it is determined that the implantable medical device will be able to operate using the first program version to deliver therapy according to the first program version if the implantable medical device was to revert back to using the first program version.

16. The system of claim 14, wherein the implantable medical device is configured to detect a problematic condition and the implantable medical device is configured to perform the reversion based on the detection of the problematic condition.

17. The system of claim 16, wherein the implantable medical device is configured to detect the problematic condition by detecting one or more errors preventing intended operation of the implantable medical device.

18. The system of claim 16, wherein the implantable medical device is configured to detect the problematic condition by receiving an external signal indicating dissatisfaction with operation of the implantable medical device.

19. The system of claim 16, wherein:
the control circuitry that is configured to determine whether the implantable medical device will be able to operate using the first program version to deliver therapy according to the first program version is located within the implantable medical device and is further configured to perform the determination based on the detection of the problematic condition; and
the implantable medical device is configured to revert from operating according to the second program version to operating according to the first program version only if the control circuitry determines that the implantable medical device is able to operate using the first program version.

20. The system of claim 14, wherein the control circuitry is further configured to:
determine which program versions of a plurality of program versions saved in memory of the implantable medical device as a plurality of restore points the implantable medical device will be able to operate to deliver therapy according to each respective program version of the plurality of program versions; and
delete or invalidate any of the plurality of restore points for which the control circuitry determines that the implantable medical device will not be able to use to operate the implantable medical device to deliver therapy according to the respective program version.

21. The system of claim 14, wherein the control circuitry is configured to determine whether the implantable medical device will be able to operate using the first program version to deliver therapy according to the first program version by at least determining whether a therapy medium of the implantable medical device that the first program version would use has changed.

22. The system of claim 14, wherein the control circuitry is configured to determine whether the implantable medical device will be able to operate using the first program version to deliver therapy according to the first program version by at least determining whether a drug stored within the implantable medical device or an electrode configuration has changed.

23. The system of claim 14, wherein the first program version includes firmware that controls the basic functions of the implantable medical device.

24. The system of claim 14, wherein the first program version includes program instructions that control therapy settings for the implantable medical device.

25. The system of claim 14, wherein the reversion of operational programming by the implantable medical device from the second program version to the first program version only restores the therapy settings of the first program version and does not change operational logic that controls the basic functions of the implantable medical device.

26. A system comprising:
    means for reprogramming an implantable medical device to operate using a second program version, the second program version replacing a first program version in controlling operation of the implantable medical device;
    means for determining whether the implantable medical device will be able to operate using the first program version to deliver therapy according to the first program version if the implantable medical device was to revert back to using the first program version; and
    means for reverting operational programming of the implantable medical device from the second program version to the first program version, the first program version saved in memory internal to the implantable medical device as a restore point while the implantable medical device operates according to the second program version between the reprogramming and reverting of the implantable medical device.

27. A non-transitory computer-readable medium comprising instructions executable by a processor to cause circuitry to:
    reprogram an implantable medical device to operate using a second program version, the second program version replacing a first program version in controlling operation of an implantable medical device;
    determine whether the implantable medical device will be able to operate using the first program version to deliver therapy according to the first program version if the implantable medical device was to revert back to using the first program version; and
    revert operational programming of the implantable medical device from the second program version to the first program version, the first program version saved in memory internal to the implantable medical device as a restore point while the implantable medical device operates according to the second program version between the reprogramming and reverting of the implantable medical device.

* * * * *